(12) United States Patent
Tanigawara et al.

(10) Patent No.: US 8,765,713 B2
(45) Date of Patent: Jul. 1, 2014

(54) METHOD FOR DETERMINATION OF SENSITIVITY TO ANTI-CANCER AGENT

(75) Inventors: Yusuke Tanigawara, Shinjuku-ku (JP); Sayo Suzuki, Shinjuku-ku (JP); Yusuke Ikoma, Shinjuku-ku (JP); Akito Nishimuta, Shinjuku-ku (JP); Tetsuya Suzuki, Shinjuku-ku (JP); Shinji Sugimoto, Minato-ku (JP)

(73) Assignees: Keio University, Tokyo (JP); Kabushiki Kaisha Yakult Honsha, Tokyo (JP)

( * ) Notice: Subject to any disclaimer, the term of this patent is extended or adjusted under 35 U.S.C. 154(b) by 30 days.

(21) Appl. No.: 13/504,985

(22) PCT Filed: Oct. 29, 2010

(86) PCT No.: PCT/JP2010/069363
§ 371 (c)(1),
(2), (4) Date: Apr. 30, 2012

(87) PCT Pub. No.: WO2011/052749
PCT Pub. Date: May 5, 2011

(65) Prior Publication Data
US 2012/0214831 A1 Aug. 23, 2012

(30) Foreign Application Priority Data

Oct. 30, 2009 (JP) ................................ 2009-250259
Feb. 1, 2010 (JP) ................................ 2010-020457

(51) Int. Cl.
| | | |
|---|---|---|
| *A61K 31/505* | (2006.01) | |
| *A61K 31/282* | (2006.01) | |
| *A61P 35/00* | (2006.01) | |
| *C40B 30/10* | (2006.01) | |
| *G01N 33/53* | (2006.01) | |
| *A61K 31/513* | (2006.01) | |
| *G01N 33/574* | (2006.01) | |
| *G01N 30/72* | (2006.01) | |

(52) U.S. Cl.
CPC ........ *A61K 31/513* (2013.01); *G01N 33/57419* (2013.01); *G01N 30/7233* (2013.01)
USPC ............ 514/50; 514/19.3; 514/274; 514/492; 435/7.9; 506/12

(58) Field of Classification Search
CPC .............. A61K 31/513; A61K 31/555; G01N 2333/4727; G01N 2800/52; G01N 33/574; G01N 33/57419; G01N 30/7233; G01N 33/6848; G01N 2291/02809
USPC ........ 514/19.3, 274, 50, 492; 435/7.9; 506/12
See application file for complete search history.

(56) References Cited

U.S. PATENT DOCUMENTS

| | | | |
|---|---|---|---|
| 7,700,280 B2 * | 4/2010 | Al-Murrani | 435/6.12 |
| 2009/0258795 A1 * | 10/2009 | Cowens et al. | 506/16 |
| 2010/0221729 A1 | 9/2010 | Al-Murrani | |
| 2010/0221730 A1 | 9/2010 | Al-Murrani | |
| 2010/0221731 A1 | 9/2010 | Al-Murrani | |
| 2010/0323034 A1 * | 12/2010 | Tanigawara et al. | 424/649 |

FOREIGN PATENT DOCUMENTS

| | | |
|---|---|---|
| CA | 2 713 296 A1 | 8/2009 |
| CN | 1922332 A | 2/2007 |
| CN | 101011351 A | 8/2007 |
| JP | 2007 517058 | 6/2007 |
| WO | 2005 007846 | 1/2005 |
| WO | WO 2005/066371 A2 | 7/2005 |
| WO | WO 2005/066371 A3 | 7/2005 |
| WO | WO 2006/060419 A2 | 6/2006 |
| WO | WO 2006/060419 A3 | 6/2006 |
| WO | WO 2007/002069 A2 | 1/2007 |
| WO | WO 2007/002069 A3 | 1/2007 |
| WO | WO 2007/071914 A1 | 6/2007 |
| WO | 2009 096196 | 8/2009 |

OTHER PUBLICATIONS

Liu et al. (Journal of Cancer Research, 19(20; pp. 94-99, 2007.*
U.S. Appl. No. 13/505,143, filed Apr. 30, 2012, Tanigawara et al.
U.S. Appl. No. 13/505,175, filed Apr. 30, 2012, Tanigawara et al.
Tanigawara, Y., "Pharmaco-proteomics and metabolomics for personalized medicine," 19th Annual Meeting of Japanese Society of Pharmaceutical Health Care and Sciences Koen Yoshishu, p. 245, S22-3 (Sep. 15, 2009).

Shirota, Y., et al., "ERCC1 and Thymidylate Synthase mRNA Levels Predict Survival for Colorectal Cancer Patients Receiving Combination Oxaliplatin and Fluorouracil Chemotherapy," Journal of Clinical Oncology, vol. 19, No. 23, pp. 4298-4304, (Dec. 1, 2001).

Stoehlmacher, J., et al., "A multivariate analysis of genomic polymorphisms: prediction of clinical outcome of 5-FU/oxaliplatin combination chemotherapy in refractory colorectal cancer," British Journal of Cancer, vol. 91, pp. 344-354, (2004).

Stoehlmacher, J., et al., "A Polymorphism of the XRCC1 Gene Predicts for Response to Platinum Based Treatment in Advanced Colorectal Cancer," Anticancer Research, vol. 21, pp. 3075-3080, (2001).

Park, D.J., et al., "A Xeroderma Pigmentosum Group D Gene Polymorphism Predicts Clinical Outcome to Platinum-based Chemotherapy in Patients with Advanced Colorectal Cancer," Cancer Research, vol. 61, pp. 8654-8658, (Dec. 15, 2001).

Fink, D., et al., "The Role of DNA Mismatch Pair in Platinum Drug Resistance," Cancer Research, vol. 56, pp. 4881-4886, (Nov. 1, 1996).

Stoehlmacher, J., et al., "Association Between Glutathione S-Transferase P1, T1, and M1 Genetic Polymorphism and Survival of Patients With Metastatic Colorectal Cancer," Journal of the National Cancer Institute, vol. 94, No. 12, pp. 936-942, (Jun. 19, 2002).

Zhang, S., et al., "Organic Cation Transporters Are Detiminants of Oxaliplatin Cytotoxicity," Cancer Research, vol. 66, No. 17, pp. 8847-8857, (Sep. 1, 2006).

Samimi, G., et al., "Modulation of the Cellular Pharmacology of Cisplatin and Its Analogs by the Copper Exporters ATP7A and ATP7B," Molecular Pharmacology, vol. 66, No. 1, pp. 25-32, (2004).

Samimi, G., et al., "Increased Expression of the Copper Efflux Transporter ATP7A Mediates Resistance to Cisplatin, Carboplatin, and Oxaliplatin in Ovarian Cancer Cells," Clinical Cancer Research, vol. 10, pp. 4661-4669, (Jul. 15, 2004).

Ruzzo, A., et al., "Pharmacogenetic Profiling in Patients with Advanced Colorectal Cancer Treated With First-Line FOLFOX-4 Chemotherapy," Journal of Clinical Oncology, vol. 25, No. 10, pp. 1247-1254, (Apr. 1, 2007).

Nadal, C., et al., "FAS/FAS Ligand Ratio: A Marker of Oxaliplatin-Based Intrinsic and Acquired Resistance in Advanced Colorectal Cancer," Clinical Cancer Research, vol. 11, No. 13, pp. 4770-4774, (Jul. 1, 2005).

Griffiths, G.J., et al., "Expression of Kinase-defective Mutants of c-Src in Human Metastatic Colon Cancer Cells Decreases Bcl-$x_L$ and Increases Oxaliplatin- and Fas-induced Apoptosis," Journal of Biological Chemistry, vol. 279, No. 44, pp. 46113-46121, (Oct. 29, 2004).

Van Kuilenburg, A.B.P., "Dihydropyrimidine dehydrogenase and the efficacy and toxicity of 5-fluorouracil," European Journal of Cancer, vol. 40, pp. 939-950, (2004).

Aschele, C., et al., "Thymidylate Synthase expression as a predictor of clinical response to fluoropyrimidine-based chemotherapy in advanced colorectal cancer," Cancer Treatment Reviews, vol. 28, pp. 27-47, (2002).

Popat, S., et al., "Thymidylate Synthase Expression and Prognosis in Colorectal Cancer: A Systematic Review and Meta-Analysis," Journal of Clinical Oncology, vol. 22, No. 3, pp. 529-536, (Feb. 1, 2004).

Braun, M.S., et al., "Predictive Biomarkers of Chemotherapy Efficacy in Colorectal Cancer: Results From the UK MRC FOCUS Trial," Journal of Clinical Oncology, vol. 26, No. 16, pp. 2690-2698, (Jun. 1, 2008).

International Search Report Issued Nov. 30, 2010 in PCT/JP10/69363 Filed Oct. 29, 2010.

Extended European Search Report issued Feb. 7, 2013, in European Patent Application No. 10826879.8.

Sayo Suzuki, et al., "S100A10 protein expression is associated with oxaliplatin sensitivity in human colorectal cancer cells", Proteome Science, vol. 9, 76, XP-002690352, Dec. 2011, 12 pages.

U.S. Appl. No. 14/007,145, filed Sep. 24, 2013, Tanigawara et al.

Combined Chinese Office Action and Search Report issued Dec. 3, 2013, in Patent Application No. 201080049208.2 (with English-language translation of summary).

* cited by examiner

*Primary Examiner* — Savitha Rao

(74) *Attorney, Agent, or Firm* — Oblon, Spivak, McClelland, Maier & Neustadt, L.L.P.

(57) ABSTRACT

A marker for determining sensitivity of a patient to an anti-cancer agent, and novel cancer therapeutic means employing the marker, wherein the marker for determining sensitivity to an anti-cancer agent is a protein or a fragment, where in the protein or a fragment thereof exhibits a peak at m/z of 5,300 to 5,400, a peak at m/z of 6,130 to 6,230, a peak at m/z of 7,000 to 7,080 a peak at m/z of 7,840 to 7,920, a peak at m/z of 8,920 to 9,000, a peak at m/z of 12,440 to 12,560, a peak at m/z of 17,100 to 17,270, a peak at m/z of 18,290 to 18,470, a peak at m/z of 24,660 to 24,750, a peak at m/z of 35,980 to 36,290, a peak at m/z of 8,650 to 8,750, a peak at m/z of 9,100 to 9,200, a peak at m/z of 11,760 to 11,890, the peaks being determined by means of a mass spectrometer.

20 Claims, 14 Drawing Sheets

METHOD FOR DETERMINATION OF SENSITIVITY TO ANTI-CANCER AGENT

This application is a National Stage of PCT/JP10/069363 filed Oct. 29, 2010 and claims the benefit of JP 2009-250259 filed Oct. 30, 2009 and JP 2010-020457 filed Feb. 1, 2010.

TECHNICAL FIELD

The present invention relates to a marker for use in determination of the sensitivity of a cancer patient to an anti-cancer agent to be administered thereto, which marker can determine whether or not the cancer of the patient has a therapeutic response to the anti-cancer agent, and to application of the marker.

BACKGROUND ART

Anti-cancer agents have various types such as an alkylating agent, a platinum agent, an antimetabolite, an antitumor antibiotic, and an antitumor plant alkaloid. These anti-cancer agents are effective for some cancers but not effective for other cancers. Even when an anti-cancer agent is confirmed to be effective for a certain cancer, the anti-cancer agent is effective for some patients and not effective for other patients, leading to interindividual differences. Whether or not a cancer of a specific patient has response to an anti-cancer agent is designated as sensitivity to the anti-cancer agent.

Oxaliplatin, (SP-4-2)-[(1R,2R)-cyclohexane-1,2-diamine-κN,κN'][ethanedioato(2-)-κO$^1$,κO$^2$]platinum (IUPAC), is a third-generation platinum-based complex anti-cancer agent. Similar to precedent drugs (cisplatin (CDDP) and carboplatin (CBDCA)), the action mechanism thereof is thought to be based on inhibition of DNA synthesis and/or protein synthesis via cross-linking with DNA bases. Oxaliplatin (L-OHP) exhibits anti-tumor effect on colorectal cancer, to which CDDP or CBDCA is ineffective, and shows different spectrum of anti-tumor activity from that of a precedent platinum-based complex anti-cancer agent. In the United States of America, oxaliplatin for use in combination with fluorouracil (5-FU) and levofolinate (LV) was approved as a first line therapy for metastatic colorectal cancer in January, 2004. In Japan, oxaliplatin was listed in the National Health Insurance (NHI) price list in the case of combination use thereof with continuous infusional fluorouracil and levofolinate (FOLFOX4 regimen) for "advanced/recurrent colorectal cancer not amenable to curative surgical resection" in April, 2005. Until the early 1990's, 5-FU/LV regimen to advanced/recurrent colorectal cancer has provided a survival of 10 to 12 months. In contrast, a FOLFOX regimen combined with oxaliplatin results in a prolonged survival of 19.5 months (about twice the survival time). In August, 2009, an indication of oxaliplatin combined with continuous infusional fluorouracil and levofolinate to "postoperative adjuvant chemotherapy for colon cancer" was added to efficacy and effectiveness. Thus, oxaliplatin is a promising drug having an efficacy in an increased number of colorectal cancer patients.

However, the response rate of FOLFOX regimen against advanced/recurrent colorectal cancer is still as low as about 50%. In other words, about half of the treated patients achieve no effects. During administration of oxaliplatin, peripheral neuropathy frequently occurs in addition to neutropenia. Although not being fatal, these adverse events are factors which make continuation of the therapy difficult. Therefore, if there is a biomarker which can predict, before start of the treatment, a patient who is expected to achieve the response (i.e., a responder) and a patient who is not expected to achieve the response (i.e., a non-responder), to thereby diagnose the therapeutic response earlier, a chemotherapy ensuring high effectiveness and high safety can be established.

There have been a number of reports on sensitivity/resistance factor with respect to platinum-based chemotherapy, but most of them are focused on cisplatin. The therapeutic response of patients to oxaliplatin, which is structurally and functionally similar to cisplatin, is thought to generally relate to, for example, the following:

1) enhancement of the ability of excising and repairing DNA damaged by oxaliplatin;

2) inactivation (detoxification) of oxaliplatin (active form) in cells; and 3) reduction in accumulation amount of oxaliplatin in cells.

In the oxaliplatin+5-FU combination therapy for colorectal cancer patients, the therapeutic response and prognosis-predicting factor are now under study on the basis of 1) to 3).

Regarding 1), the excision repair cross-complementing group 1 (ERCC1) gene expression level in tumor cells is reported to serve as a prognosis factor, the ERCC1 playing an important role in nucleotide excision repair (NER) (Non-Patent Document 1). Patients having a C/C homozygote of C118T (a type of single nucleotide polymorphism (SNP) of ERCC1) exhibit a survival longer than that of patients having at least one T allele (Non-Patent Document 2). In Xeroderma pigmentosum D (XPD, also known as ERCC2), a genetic polymorphism involving Lys751Gln amino acid mutation is reported to relate to percent tumor reduction and survival (Non-Patent Documents 2 and 3). In base excision repair (BER), there has been reported a relationship between the tumor reduction effect and a genetic polymorphism involving Arg399Gln amino acid mutation in X-ray repair cross-complementing group 1 (XRCC1) encoding a protein relating to effective repair of DNA single strand breakage caused by exposure to an alkylating agent or the like (Non-Patent Document 4). However, further analysis of the same patients has revealed that the genetic polymorphism does not affect the clinical prognosis (Non-Patent Document 2). DNA mismatch repair (MMR) is thought to relate to lowering sensitivity to cisplatin. However, in vitro studies have revealed that MMR does not involve repair of DNA damaged by oxaliplatin (Non-Patent Document 5).

Regarding 2), glutathione-S-transferase (GST) is an enzyme which catalyzes phase II reaction in the detoxification and metabolism. GST catalyzes formation of a conjugation of a DNA-platinum adduct and glutathione, to thereby inactivate a drug. Among GST subtypes, GSTP1 has a high expression level in colorectal cancer, and a genetic polymorphism involving Ile105Val amino acid mutation relates to survival (median survival: Ile/Ile 7.9 months, Ile/Val 13.3 months, Val/Val 24.9 months) (Non-Patent Document 6).

Regarding 3), studies employing cultured cells have revealed that organic cation transporters (OCTs) relate to transportation of oxaliplatin into cells and sensitivity to oxaliplatin (Non-Patent Document 7). A relationship between copper- and heavy-metal-transporters such as ATP7A and ATP7B and sensitivity has also been reported (Non-Patent Documents 8 and 9). However, the relationship between expression of these transporters and therapeutic response to oxaliplatin has not been clinically elucidated.

Recent clinical studies for advanced colorectal cancer patients having received FOLFOX regimen have revealed that a genetic polymorphism of ERCC1 (Asn118Asn) and that of XPD (Lys751Gln) independently relate to progression-free survival (PFS), and that a genetic polymorphism of GSTP1 (Ile105Val) does not relate to PFS but tends to have a relationship with oxaliplatin-induced neurotoxicity (Non-Patent Document 10).

In vitro studies have revealed a number of resistance-related factors of cisplatin (a precedent platinum-based complex drug), and the relationship between oxaliplatin and apoptosis-related factors such as FAS/FASL and Bcl-xL have been reported (Non-Patent Documents 11 and 12). However, oxaliplatin exhibits a therapeutic response differing from that of cisplatin, depending on the type of cancer. In addition, there has not been substantially elucidated the cell response of cancer cells with respect to a platinum-DNA adduct, which exerts cytotoxic activity of oxaliplatin. Thus, there has been established no definite biomarker which can predict the therapeutic response to chemotherapy employing oxaliplatin.

Meanwhile, fluorouracil is a fluoro-pyrimidine anti-cancer agent developed in 1957 and even now serves as a basic drug for use in the chemotherapy of gastrointestinal cancer. When incorporated into cancer cells, fluorouracil exerts cytotoxic effect through a principle action mechanism of DNA synthesis inhibition induced by inhibition of thymidylate synthase (TS) by an active metabolite, fluorodeoxyuridine-5'-monophosphate (FdUMP), and another mechanism of RNA function inhibition by an active metabolite, 5-fluorouridine triphosphate (FUTP).

Hitherto, many studies have been conducted to predict therapeutic response to fluoro-pyrimidine anti-cancer agents. In particular, many studies have been focused on dihydropyrimidine dehydrogenase (DPD), which is a fluorouracil degrading enzyme, and thymidylate synthase (TS), which is a target enzyme of an active metabolite. A tumor in which DPD, a rate-limiting enzyme in the catabolism of fluorouracil, is highly expressed is reported to have resistance to fluorouracil (Non-Patent Document 13), but a limited number of studies have been conducted with clinical specimens. The TS expression level is reported to be a possible factor that determines the therapeutic effect by a fluoro-pyrimidine anti-cancer agent, even when the expression level is determined through any assay method such as the enzymatic activity method, protein level assay, or RNA level assay (Non-Patent Documents 14 and 15). However, the above-obtained results are not completely the same, and there has been known no definite biomarker which can predict the therapeutic response to fluorouracil in an early treatment stage.

In metastatic colorectal cancer patients having fluorouracil resistance, ERCC1 and TS mRNA expression levels in tumor cells are reported to serve as factors that predict therapeutic response to 5-FU/L-OHP combination therapy (Non-Patent Document 16). However, recently, large-scale prospective clinical trial (FOCUS trial) for investigating biomarkers that predict therapeutic response of advanced colorectal cancer patients to chemotherapy has revealed that ERCC1 does not serve as a significant predictive factor for 5-FU/L-OHP combination therapy, and that only topoisomerase-1 (Topo1) exhibits weak relationship thereto (Non-Patent Document 17). This indicates that there has been established no biomarker that can reliably select a patient who is expected to be effectively treated through the 5-FU/L-OHP combination therapy. Furthermore, since the therapy schedule of cancer chemotherapy generally requires a long period of time, continuous monitoring of sensitivity of a target patient to a target anti-cancer agent during the therapy can determine whether or not the therapy should be continued. Thus, such monitoring is thought to be meritorious from the viewpoints of reduction or mitigation of the burden on patients and adverse events, leading to reduction in medical cost. Therefore, there is keen demand for establishment of a biomarker that can predict the effect of 5-FU, L-OHP, or a combination of 5-FU/L-OHP or that can determine therapeutic response in an early stage, for the purpose of predicting therapeutic response of individual patients and establishing diagnosis in an early stage to select an appropriate drug and treatment regimen; i.e., for realizing "personalized therapy."

PRIOR ART DOCUMENTS

Non-Patent Documents

Non-Patent Document 1: J. Clin. Oncol. 19, 4298-4304 (2001)
Non-Patent Document 2: Br. J. Cancer 91, 344-354 (2004)
Non-Patent Document 3: Cancer Res. 61, 8654-8658 (2001)
Non-Patent Document 4: Anticancer Res. 21, 3075-3079 (2001)
Non-Patent Document 5: Cancer Res. 56, 4881-4886 (1996)
Non-Patent Document 6: J. Natl. Cancer Inst. 94, 936-942 (2002)
Non-Patent Document 7: Cancer Res. 66, 8847-8857 (2006)
Non-Patent Document 8: Mol. Pharmacol. 66, 25-32 (2004)
Non-Patent Document 9: Clin. Cancer Res. 10, 4661-4669 (2004)
Non-Patent Document 10: J. Clin. Oncol. 25, 1247-1254 (2007)
Non-Patent Document 11: Clin. Cancer Res. 11, 4770-4774 (2005)
Non-Patent Document 12: J. Biol. Chem. 279, 46113-46121 (2004)
Non-Patent Document 13: European Journal of Cancer 2004; 40: 939-950
Non-Patent Document 14: Cancer Treatment Reviews 2002; 28: 27-47
Non-Patent Document 15: J. Clin. Oncol. 2004; 22: 529-536
Non-Patent Document 16: J. Clin. Oncol. 2001; 19: 4298-4304
Non-Patent Document 17: J. Clin. Oncol. 2008; 26: 2690-2698

SUMMARY OF THE INVENTION

Problems to be Solved by the Invention

An object of the present invention is to provide a marker for determining sensitivity of a patient to an anti-cancer agent, which marker can determine whether or not the patient has a therapeutic response to the anti-cancer agent. Another object is to provide novel cancer therapeutic means employing the marker.

Means for Solving the Problems

In order to attain the aforementioned objects, the present inventors have searched for a marker for determining sensitivity to an anti-cancer agent by culturing human cancer cells, exposing the cells to a drug, and comprehensively analyzing the time-dependent expression profiles of intracellular proteins after exposure to the drug by means of a surface-enhanced laser desorption/ionization time-of-flight mass spectrometer (SELDI-TOF MS). More specifically, two types of human colorectal cancer cells, one having high sensitivity to 5-FU, L-OHP, and combination of 5-FU/L-OHP and the other having low sensitivity thereto, were exposed to 5-FU (single drug), L-OHP (single drug), or 5-FU/L-OHP (combination), and the time-dependent expression profiles of intracellular proteins after exposure to the drug were investigated. As a result, the inventors have found, after exposure to 5-FU, several proteins exhibiting time-dependent intracellular expression level profiles which differ between high-sensitivity cells and low-sensitivity cells. These proteins or fragments thereof have been detected as a peak at m/z, as determined by means of a mass spectrometer, of 5,300 to 5,400, 6,130 to 6,230, 7,000 to 7,080, 7,840 to 7,920, 17,100 to 17,270, 18,290 to 18,470, 24,660 to 24,750, 35,980 to 36,290, or 9,100 to 9,200, or identified as a calcium-binding protein S100A10.

Similarly, the inventors have found, after exposure to L-OHP, several proteins exhibiting time-dependent intracellular expression level profiles which differ between high-sensitivity cells and low-sensitivity cells. These proteins or fragments thereof have been detected as a peak at m/z, as determined by means of a mass spectrometer, of 5,300 to 5,400, 6,130 to 6,230, 7,000 to 7,080, 7,840 to 7,920, 12,440 to 12,560, 17,100 to 17,270, 18,290 to 18,470, 24,660 to 24,750, 35,980 to 36,290, or 9,100 to 9,200.

Furthermore, the inventors have found, after exposure to 5-FU/L-OHP in combination, several proteins exhibiting time-dependent intracellular expression level profiles which differ between high-sensitivity cells and between low-sensitivity cells. These proteins or fragments thereof have been detected as a peak at m/z, as determined by means of a mass spectrometer, peak of 5,300 to 5,400, 6,130 to 6,230, 7,000 to 7,080, 7,840 to 7,920, 8,920 to 9,000, 12,440 to 12,560, 17,100 to 17,270, 18,290 to 18,470, 24,660 to 24,750, 35,980 to 36,290, or 9,100 to 9,200, or identified as a calcium-binding protein S100A10.

Separately, the inventors have found, before exposure to any of these drugs, several proteins exhibiting intracellular expression levels which differ between high-sensitivity cells and low-sensitivity cells. These proteins or fragments thereof have been detected as a peak at m/z, as determined by means of a mass spectrometer, of 6,130 to 6,230, 17,100 to 17,270, 8,650 to 8,750, or 11,760 to 11,890.

On the basis of these findings, the inventors have carried out further studies, and have found that whether or not a cancer of a target cancer patient has a sensitivity to 5-FU therapy, L-OHP therapy, or 5-FU/L-OHP combination therapy can be determined through measuring the relevant protein level of a biological sample derived from the cancer patient; that screening of an anti-cancer agent sensitivity enhancer can be accomplished through employment of variation in expression of the substance as an index; and that the therapeutic effect of the relevant anti-cancer agent can be drastically enhanced by use, in combination, of the anti-cancer agent sensitivity enhancer and the anti-cancer agent which is a sensitivity enhancement target of the enhancer. The present invention has been accomplished on the basis of these findings.

Accordingly, the present invention provides a marker for determining sensitivity to an anti-cancer agent, the marker comprising a protein selected from the group consisting of a protein or a fragment thereof which is detected as a peak at m/z of 5,300 to 5,400 (hereinafter referred to as protein A), a protein or a fragment thereof which is detected as a peak at m/z of 6,130 to 6,230 (hereinafter referred to as protein B), a protein or a fragment thereof which is detected as a peak at m/z of 7,000 to 7,080 (hereinafter referred to as protein C), a protein or a fragment thereof which is detected as a peak at m/z of 7,840 to 7,920 (hereinafter referred to as protein D), a protein or a fragment thereof which is detected as a peak at m/z of 8,920 to 9,000 (hereinafter referred to as protein E), a protein or a fragment thereof which is detected as a peak at m/z of 12,440 to 12,560 (hereinafter referred to as protein G), a protein or a fragment thereof which is detected as a peak at m/z of 17,100 to 17,270 (hereinafter referred to as protein H), a protein or a fragment thereof which is detected as a peak at m/z of 18,290 to 18,470 (hereinafter referred to as protein I), a protein or a fragment thereof which is detected as a peak at m/z 24,660 to 24,750 (hereinafter referred to as protein J), a protein or a fragment thereof which is detected as a peak at m/z of 35,980 to 36,290 (hereinafter referred to as protein K), a protein or a fragment thereof which is detected as a peak at m/z of 8,650 to 8,750 (hereinafter referred to as protein L), a protein or a fragment thereof which is detected as a peak at m/z of 9,100 to 9,200 (hereinafter referred to as protein M), and a protein or a fragment thereof which is detected as a peak at m/z of 11,760 to 11,890 (hereinafter referred to as protein N), the peaks being determined by means of a mass spectrometer.

The present invention also provides a marker for determining sensitivity to an anti-cancer agent containing fluorouracil or a salt thereof or a combination of fluorouracil or a salt thereof and oxaliplatin or a salt thereof, the marker comprising a calcium-binding protein S100A10 (hereinafter referred to as protein F).

The present invention also provides a method for determining sensitivity of a subject to an anti-cancer agent, the method comprising measuring the level of any of proteins A to N in a specimen derived from the subject.

The present invention also provides a kit for carrying out the method for determining sensitivity of a subject to an anti-cancer agent, the kit comprising a protocol for measuring the level of any of proteins A to N in a specimen derived from the subject.

The present invention also provides a screening method for an anti-cancer agent sensitivity enhancer, the method comprising employing variation in expression of any of the proteins A to N as an index.

The present invention also provides an anti-cancer agent sensitivity enhancer obtained through the screening method.

The present invention also provides a composition for cancer therapy comprising, in combination, the anti-cancer agent sensitivity enhancer and an anti-cancer agent which is a sensitivity enhancement target of the enhancer.

The present invention also provides the proteins A to N for use in determining the anti-cancer agent sensitivity.

Effects of the Invention

According to the marker for determining sensitivity to an anti-cancer agent of the present invention, the sensitivity to an anti-cancer agent of a patient can be appropriately determined before the therapy or in an early stage after start of the therapy. As a result, an anti-cancer agent having higher therapeutic effect can be selected, and unnecessary adverse events, which would otherwise result from administration of an anti-cancer agent exerting no expected therapeutic effect, can be prevented. Meanwhile, the therapy schedule employing an anti-cancer agent generally requires a long period of time. Even in on-going therapy, the sensitivity of the target cancer to an anti-cancer agent can be evaluated in a time-dependent manner through determination of the anti-cancer agent sensitivity in each therapy cycle, whereby a determination can be made on whether or not the therapy should be continued. As a result, progression of cancer and aggravation of adverse events, which would otherwise result from continuous administration of an anti-cancer agent exerting no expected therapeutic effect, can be prevented. Thus, reductions can be expected in the burden on patients and medical cost.

In addition, when the marker of the present invention is used, a drug which can promote anti-cancer agent sensitivity can be selected through screening. Thus, through employment, in combination, of the target anti-cancer agent and an anti-cancer agent sensitivity enhancer to the anti-cancer agent, the expected cancer therapeutic effect can be drastically enhanced. The assay reagent for measuring the marker for determining sensitivity to an anti-cancer agent of the present invention is useful as an reagent for determining sensitivity to an anti-cancer agent.

MODES FOR CARRYING OUT THE INVENTION

Figure 1:
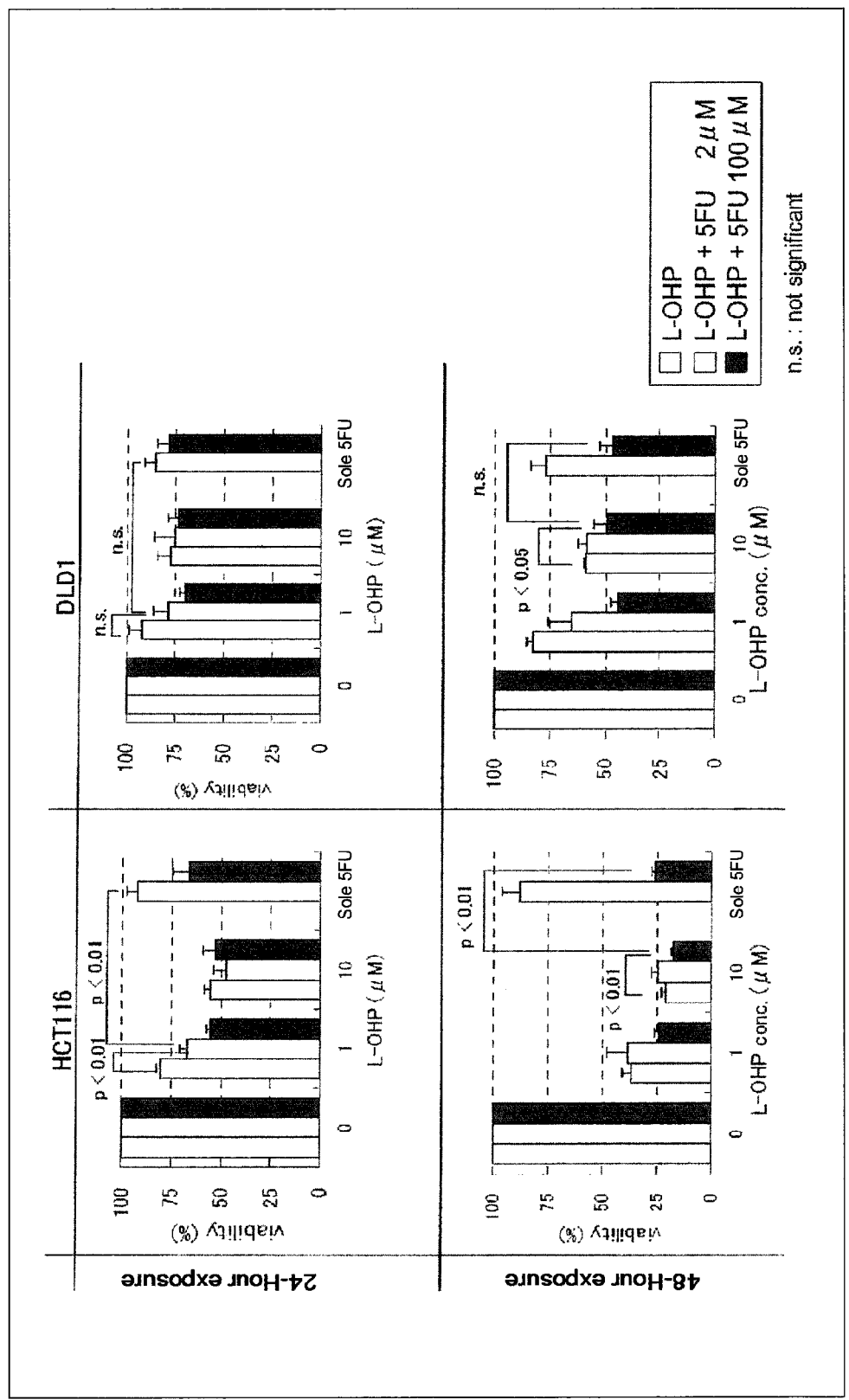
FIG. 1 Graphs showing the survival (%) of HCT116 cells under exposure to 5-FU, L-OHP, or 5-FU/L-OHP, and graphs showing the survival (%) of DLD-1 cells under exposure to 5-FU, L-OHP, or 5-FU/L-OHP.
Figure 2:
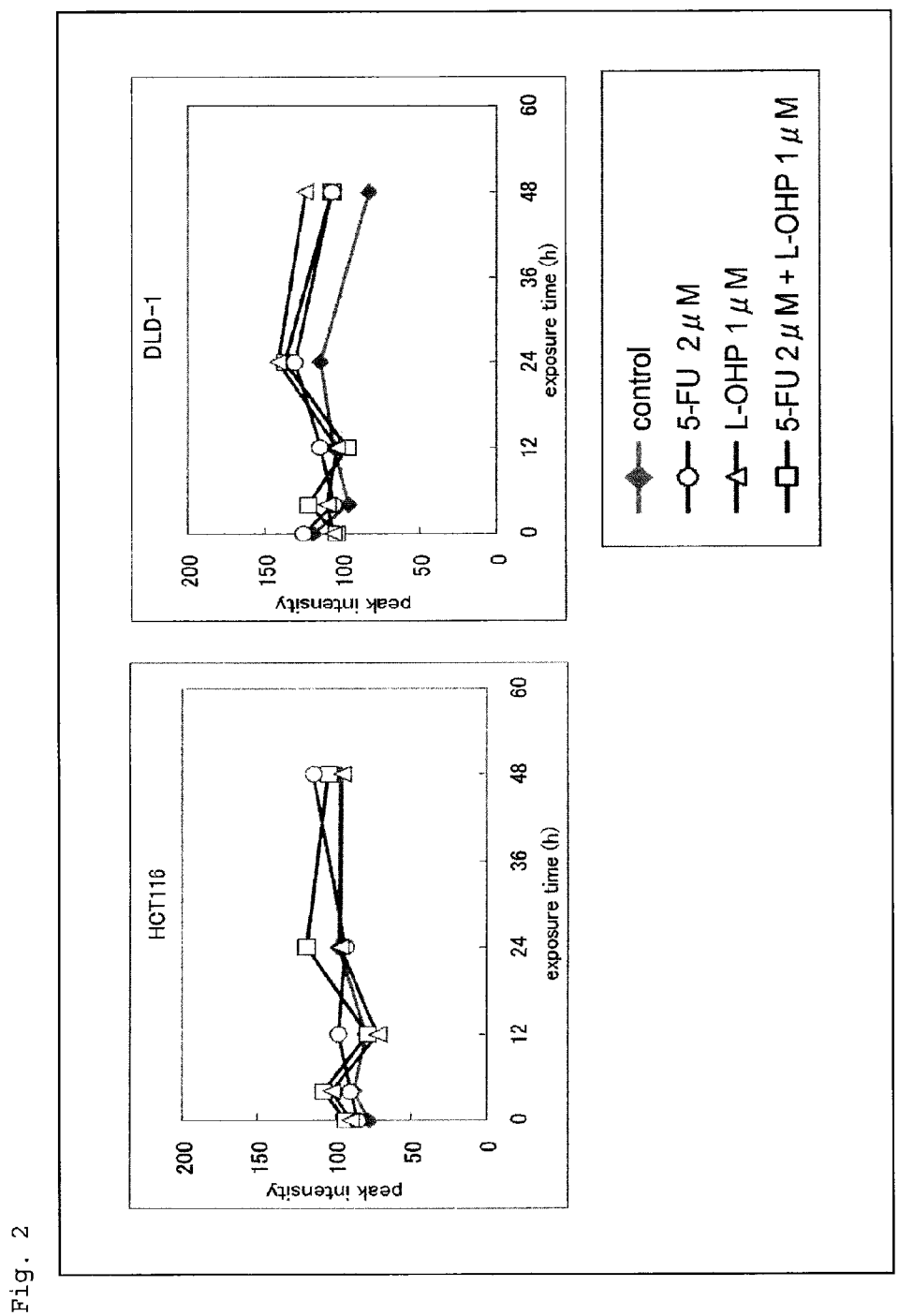
FIG. 2 A graph showing a time-dependent profile of the intracellular protein A level in HCT116 cells after exposure to 5-FU, L-OHP, or 5-FU/L-OHP, and a graph showing the time-dependent profile of the intracellular protein A level in DLD-1 cells after exposure to 5-FU, L-OHP, or 5-FU/L-OHP.
Figure 3:
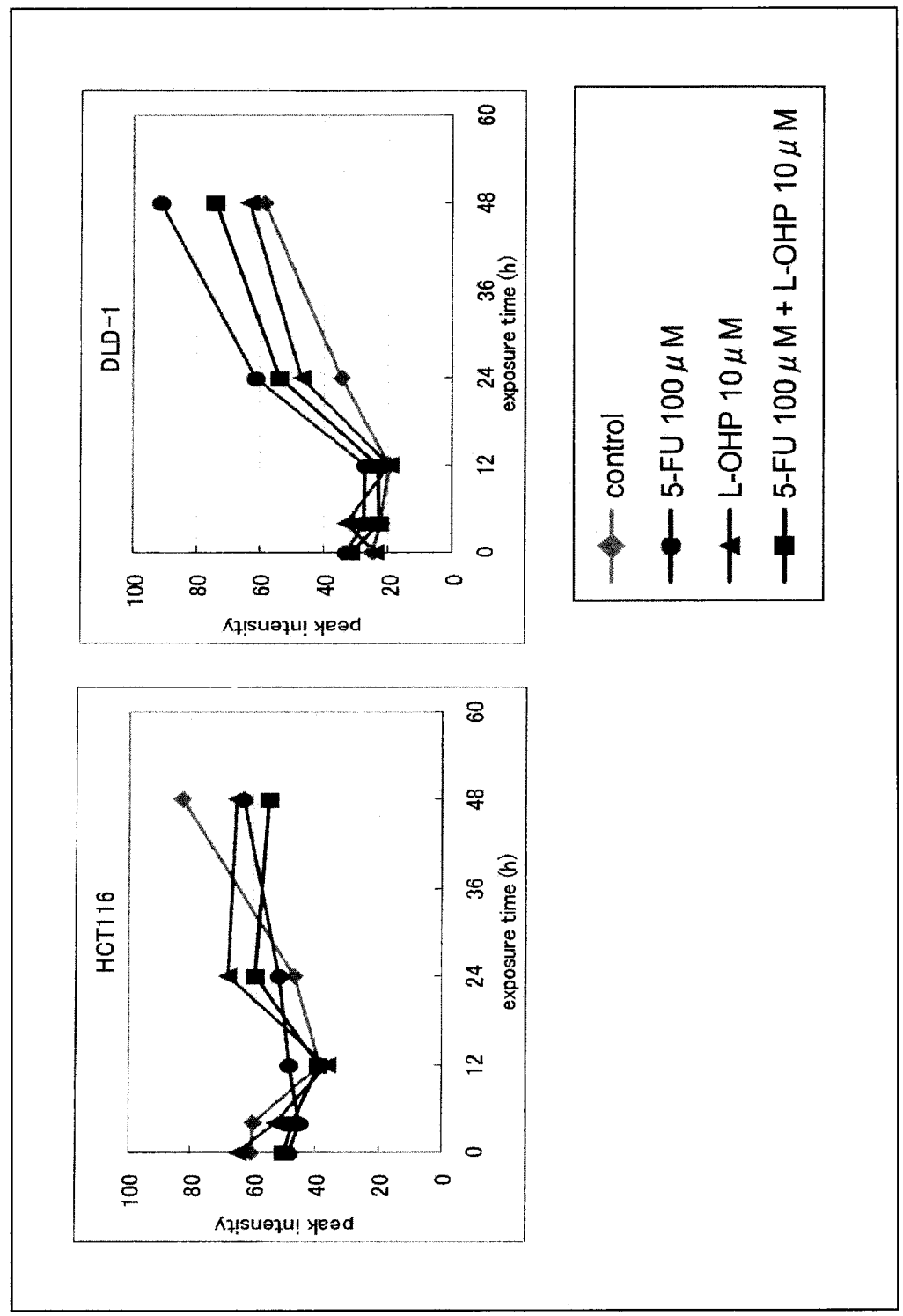
FIG. 3 A graph showing a time-dependent profile of the intracellular protein B level in HCT116 cells after exposure to 5-FU, L-OHP, or 5-FU/L-OHP, and a graph showing a time-dependent profile of the intracellular protein B level in DLD-1 cells after exposure to 5-FU, L-OHP, or 5-FU/L-OHP.
Figure 4:
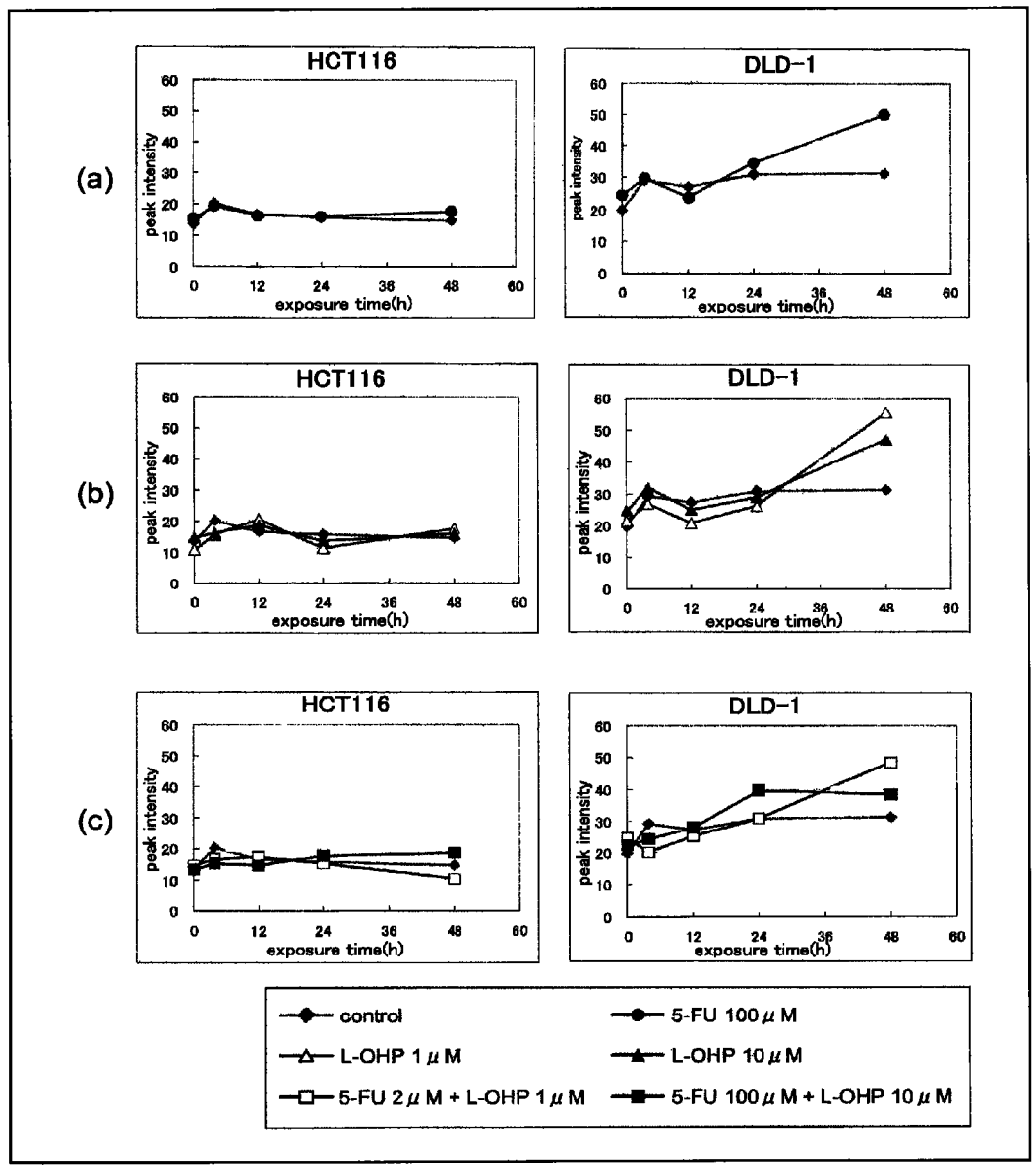
FIG. 4 Graphs showing a time-dependent profile of the intracellular protein C level in HCT116 cells after exposure to 5-FU, L-OHP, or 5-FU/L-OHP, and graphs showing a time-dependent profile of the intracellular protein C level in DLD-1 cells after exposure to 5-FU, L-OHP, or 5-FU/L-OHP.

The marker for determining sensitivity to an anti-cancer agent of the present invention is any of proteins A to N. More specifically, the proteins are detected by means of a cation-exchange chip at a pH of 4.5, and m/z peaks are determined by means of a surface-enhanced laser desorption/ionization time-of-flight mass spectrometer (SELDI-TOF MS). Thus, the proteins are a protein or a fragment thereof which is detected as a peak at m/z of 5,300 to 5,400 (protein A), a protein or a fragment thereof which is detected as a peak at m/z of 6,130 to 6,230 (protein B), a protein or a fragment thereof which is detected as a peak at m/z of 7,000 to 7,080 (protein C), a protein or a fragment thereof which is detected as a peak at m/z of 7,840 to 7,920 (protein D), a protein or a fragment thereof which is detected as a peak at m/z of 8,920 to 9,000 (protein E), a protein or a fragment thereof which is detected as a peak at m/z of 11,020 to 11,120 (protein F), a protein or a fragment thereof which is detected as a peak at m/z of 12,440 to 12,560 (protein G), a protein or a fragment thereof which is detected as a peak at m/z of 17,100 to 17,270 (protein H), a protein or a fragment thereof which is detected as a peak at m/z of 18,290 to 18,470 (protein I), a protein or a fragment thereof which is detected as a peak at m/z of 24,660 to 24,750 (protein J), a protein or a fragment thereof which is detected as a peak at m/z of 35,980 to 36,290 (protein K), a protein or a fragment thereof which is detected as a peak at m/z of 8,650 to 8,750 (protein L), a protein or a fragment thereof which is detected as a peak at m/z of 9,100 to 9,200 (protein M), and a protein or a fragment thereof which is detected as a peak at m/z of 11,760 to 11,890 (protein N), the peaks being determined by means of the mass spectrometer.

As shown in the Examples described hereinbelow, protein F has been identified as calcium-binding protein S100A10. S100A10 is known to be a member of the S100 protein family having calcium-binding EF-hand motif. S100A10 is also known to form hetero-tetramer from S100A10 dimer and Annexin A2 (Annexin-2, Annexin II, Lipocortin II, Calpactin I heavy chain, Chromobindin-8, p36, Protein I, Placental anticoagulant protein IV, or PAP-IV) dimer. Therefore, similar to S100A10, Annexin A2 may be possibly employed as a marker for determining sensitivity to an anti-cancer agent.

As shown in the Examples described hereinbelow, through investigation of intracellular protein expression in cultured cancer cells by means of a SELDI-TOF MS, levels of proteins A to C, F, and H to K were found to increase in DLD-1 cells, which are low-sensitive to 5-FU, after exposure to 5-FU. In contrast, no significant difference was observed in HCT116 cells, which are high-sensitive to 5-FU. Therefore, proteins A to C, F, and H to K are useful as markers for determining sensitivity to an anti-cancer agent, particularly as markers for determining sensitivity to 5-FU.

As shown in the Examples described hereinbelow, levels of proteins D and M were found to decrease in HCT116 cells, which are high-sensitive to 5-FU, after exposure to 5-FU. In contrast, no significant difference was observed in DLD-1 cells, which are low-sensitive to 5-FU. Therefore, proteins D and M are useful as markers for determining sensitivity to an anti-cancer agent, particularly as markers for determining sensitivity to 5-FU.

As shown in the Examples described hereinbelow, levels of proteins A to C and G to K were found to increase in DLD-1 cells, which are low-sensitive to L-OHP, after exposure to L-OHP. In contrast, no significant difference was observed in HCT116 cells, which are high-sensitive to L-OHP. Therefore, proteins A to C and G to K are useful as markers for determining sensitivity to an anti-cancer agent, particularly as markers for determining sensitivity to L-OHP.

Notably, the present inventors previously disclosed that protein F (calcium-binding protein S100A10) can be used as a marker for determining sensitivity to L-OHP in a precedent patent application (WO 2009/96196) of the same inventors. The same results were also obtained in the Examples of the present invention.

As shown in the Examples described hereinbelow, levels of proteins D and M were found to decrease in HCT116 cells, which are high-sensitive to L-OHP, after exposure to L-OHP. In contrast, no significant difference was observed in DLD-1 cells, which are low-sensitive to L-OHP. Therefore, proteins D and M are useful as markers for determining sensitivity to an anti-cancer agent, particularly as markers for determining sensitivity to L-OHP.

As shown in the Examples described hereinbelow, levels of proteins A to C, F, and H to K were found to increase in DLD-1 cells, which are low-sensitive to 5-FU/L-OHP combination, after exposure to 5-FU/L-OHP combination. In contrast, no significant difference was observed in HCT116 cells, which are high-sensitive to 5-FU/L-OHP combination. Therefore, proteins A to C, F, and H to K are useful as markers for determining sensitivity to an anti-cancer agent, particularly as markers for determining sensitivity to 5-FU/L-OHP combination. As described above, there has been known that protein F is a useful marker for determining sensitivity to L-OHP. However, it is a new finding by the present inventors that protein F serves as a useful marker for determining sensitivity to an anti-cancer agent when 5-FU/L-OHP combination is employed.

As shown in the Examples described hereinbelow, levels of proteins E and G were found to increase in HCT116 cells, which are high-sensitive to 5-FU/L-OHP combination, after exposure to 5-FU/L-OHP combination. In contrast, no significant difference was observed in DLD-1 cells, which are low-sensitive to 5-FU/L-OHP combination. Therefore, proteins E and G are useful as markers for determining sensitivity to an anti-cancer agent, particularly as markers for determining sensitivity to 5-FU/L-OHP combination.

As shown in the Examples described hereinbelow, levels of proteins D and M were found to decrease in HCT116 cells, which are high-sensitive to 5-FU/L-OHP combination, after exposure to 5-FU/L-OHP combination. In contrast, no significant difference was observed in DLD-1 cells, which are low-sensitive to 5-FU/L-OHP combination. Therefore, proteins D and M are useful as markers for determining sensitivity to an anti-cancer agent, particularly as markers for determining sensitivity to 5-FU/L-OHP combination.

As shown in the Examples described hereinbelow, levels of proteins B, H, L, and N in HCT116 cells, which are high-sensitive to 5-FU, L-OHP, and 5-FU/L-OHP combination, before exposure to any of the drugs (not exposed) were significantly higher than those in DLD-1 cells, which are low-sensitive to the aforementioned drugs. Therefore, proteins B, H, L, and N are useful as markers for determining sensitivity to an anti-cancer agent, particularly as markers for determining sensitivity to 5-FU, L-OHP, or 5-FU/L-OHP combination.

No particular limitation is imposed on the anti-cancer agent to which the marker for determining sensitivity to an anti-cancer agent of the present invention is applied. Examples of the anti-cancer agent include oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, irinotecan, irinotecan active metabolite (SN-38), nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab/ozogamicin, bortezomib, erlotinib, cetuximab, bevacizumab, sunitinib, sorafenib, dasatinib, panitumumab, asparaginase, tretinoin, arsenic trioxide, salts thereof, and active metabolites thereof. Among them, fluoro-pyrimidine anti-cancer agents and platinum-based complex anti-cancer agents are preferred, with fluorouracil, oxaliplatin, and salts thereof being particularly preferred. The marker of the present invention is preferably applied to a combination of fluorouracil or a salt thereof and oxaliplatin or a salt thereof.

In order to determine sensitivity of a subject to an anti-cancer agent by use of the marker for determining sensitivity to an anti-cancer agent of the present invention, any of the protein A level to protein N level in a specimen may be measured. Examples of the specimen include biological samples derived from subjects having cancer (i.e., cancer patients) such as blood, serum, plasma, cancer tissue biopsy specimens, cancer isolated preparations, feces, urine, ascitic fluid, pleural fluid, cerebrospinal fluid, and expectoration. Of these, serum is particularly preferred.

Examples of the target cancer of the present invention include lip, oral, pharyngeal cancers such as pharyngeal cancer; gastrointestinal cancers such as esophageal cancer, gastric cancer, and colorectal cancer; respiratory and intrathoracic organ cancers such as lung cancer; bone cancer and articular cartilage cancer; skin melanoma, squamous cell cancer, and other skin cancers; mesothelial and soft tissue cancers such as mesothelioma; female genital cancers such as breast cancer, uterine cancer, and ovarian cancer; male genital cancers such as prostate cancer; urinary tract cancers such as bladder cancer; eye, brain, and central nervous system cancers such as brain tumor; thyroid and other endocrine cancers; lymphoid tissue, hematopoietic tissue, and related tissue cancers such as non-Hodgkin's lymphoma and lymphoid leukemia; and metastatic cancers from these cancers as primary lesions. The present invention is particularly preferably applied to gastric cancer and colorectal cancer.

Proteins A to N contained in a specimen may be measured through, for example, SELDI-TOF MS or immunoassay.

Measurement through SELDI-TOF MS may be performed through the procedure as described in the Examples. In the immunoassay techniques, an immunoassay employing anti-protein A antibody to anti-protein N antibody are preferably employed. The employed anti-protein A antibody to anti-protein N antibody may be a monoclonal or polyclonal antibody. Specific examples of the immunoassay include radioimmunoassay, enzyme immunoassay, fluorescent immunoassay, luminescent immunoassay, immunoprecipitation, immunonephelometry, Western blotting, immunostaining, and immunodiffusion. Among them, Western blotting and enzyme immunoassay are preferably employed. Western blotting and enzyme-linked immunosorbent assay (ELISA) (e.g., sandwich ELISA) are particularly preferred.

In the case where proteins A to C, F, and H to K are employed and 5-FU is a target anti-cancer agent, the sensitivity of the target cancer to the anti-cancer agent is determined as follows. The level of any of the proteins in a biological sample derived from a cancer patient is measured before and after administration of the anti-cancer agent. When the protein level increases after administration of the anti-cancer agent, the cancer is determined to have no sensitivity to the anti-cancer agent, whereas when the protein level is constant or decreases after administration of the anti-cancer agent, the cancer is determined to have sensitivity to the anti-cancer agent. Specifically, when the level of any of proteins A to C, F, and H to K is lower than a predetermined standard level in an early stage after administration of the anti-cancer agent, the cancer can be determined to have sensitivity to the anti-cancer agent. Thus, the proteins may be employed as a marker for indicating that the patient is expected to receive therapeutic effect and may positively undergo continuous therapy employing the anti-cancer agent.

When the level of any of proteins A to C, F, and H to K is higher than a predetermined standard level in an early stage after administration of the anti-cancer agent, the cancer can be determined to have no sensitivity to the anti-cancer agent. When the cancer has no sensitivity to the anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to avoid progression of cancer and aggravation of adverse events which would otherwise be caused by continuous administration of an ineffective anti-cancer agent.

In the case where proteins A to C, and G to K are employed and L-OHP is a target anti-cancer agent, or where proteins A to C, F, and H to K are employed and 5-FU/L-OHP combination is a target anti-cancer agent, the sensitivity of the target cancer to the anti-cancer agent is determined in the same manner as described above.

In the case where proteins D and M are employed and 5-FU is a target anti-cancer agent, the sensitivity of the target cancer to the anti-cancer agent is determined as follows. The level of any of the proteins in a biological sample derived from a cancer patient is measured before and after administration of the anti-cancer agent. When the protein level decreases after administration of the anti-cancer agent, the cancer is determined to have sensitivity to the anti-cancer agent, whereas when the protein level is constant or increases after administration of the anti-cancer agent, the cancer is determined to have no sensitivity to the anti-cancer agent. Specifically, when the level of any of proteins D and M is lower than a predetermined standard level in an early stage after administration of the anti-cancer agent, the cancer can be determined to have sensitivity to the anti-cancer agent. Thus, the proteins may be employed as a marker for indicating that the patient is expected to receive therapeutic effect and may positively undergo continuous therapy employing the anti-cancer agent.

When the level of any of proteins D and M is higher than a predetermined standard level in an early stage after administration of the anti-cancer agent, the cancer can be determined to have no sensitivity to the anti-cancer agent. When the cancer has no sensitivity to the anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to avoid progression of cancer and aggravation of adverse events which would otherwise be caused by continuous administration of an ineffective anti-cancer agent.

In the case where proteins D and M are employed and L-OHP is a target cancer agent or 5-FU/L-OHP combination is a target anti-cancer agent, the sensitivity of the target cancer to the anti-cancer agent is determined in the same manner as described above.

In the case where proteins E and G are employed and 5-FU/L-OHP combination is a target anti-cancer agent, the sensitivity of the target cancer to the anti-cancer agent is determined as follows. The level of any of the proteins in a biological sample derived from a cancer patient is measured before and after administration of the anti-cancer agent. When the protein level increases after administration of the anti-cancer agent, the cancer is determined to have sensitivity to the anti-cancer agent, whereas when the protein level is constant or decreases after administration of the anti-cancer agent, the cancer is determined to have no sensitivity to the anti-cancer agent. Specifically, when the level of any of proteins E and G is higher than a predetermined standard level in an early stage after administration of the anti-cancer agent, the cancer can be determined to have sensitivity to the anti-cancer agent. Thus, the proteins may be employed as a marker for indicating that the patient is expected to receive therapeutic effect and may positively undergo continuous therapy employing the anti-cancer agent.

When the level of any of proteins E and G is lower than a predetermined standard level in an early stage after administration of the anti-cancer agent, the cancer can be determined to have no sensitivity to the anti-cancer agent. When the cancer has no sensitivity to the anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to avoid progression of cancer and aggravation of adverse events which would otherwise be caused by continuous administration of an ineffective anti-cancer agent.

In the case where proteins B, H, L, and N are employed and 5-FU, L-OHP, or 5-FU/L-OHP combination is a target anti-cancer agent, the sensitivity of the target cancer to the anti-cancer agent is determined as follows. The level of any of the proteins in a biological sample derived from a cancer patient is measured before administration of the anti-cancer agent. When the level of any of these proteins is lower than a predetermined standard level, the cancer can be determined to have no sensitivity to the anti-cancer agent. In the case where the cancer has no sensitivity to the target anti-cancer agent, conceivably, no pharmaceutical effect is expected, and merely adverse events caused by the anti-cancer agent occur. Thus, the marker for determining sensitivity to an anti-cancer agent of the present invention may be employed to avoid occurrence of unnecessary adverse events as well as to avoid progression of cancer and aggravation of adverse events which would otherwise be caused by continuation of ineffective therapy.

In contrast, when the level of any of these proteins is higher than a predetermined standard level, the cancer can be determined to have sensitivity to the anti-cancer agent. Thus, the proteins may also be employed as a marker for positively selecting a patient who is expected to receive therapeutic effect.

Regarding proteins B and H, when any of the protein is employed as a marker for use during administration of the anti-cancer agent, in the case where the protein level is constant or decreases after administration, the cancer can be determined to have sensitivity to the anti-cancer agent, whereas when any of the protein is employed as a marker for use before administration of the anti-cancer agent, in the case where the protein level is lower than a predetermined level, the cancer can be determined to have no sensitivity to the anti-cancer agent. Since the marker (protein B or H) plays different roles between during administration of the anti-cancer agent and before administration thereof, the marker is preferably employed in consideration of the difference.

In order to carry out the method of the present invention for determining sensitivity of a subject to an anti-cancer agent, preferably, a kit containing a protocol for measuring the level of proteins A to N of a specimen is employed. The kit contains a reagent for measuring any of proteins A to N, an indication of an instruction manual for use of the reagent, standards for determining the presence or absence of sensitivity to the anti-cancer agent, etc. The standards include standard levels of proteins A to N, a high threshold level, a low threshold level, factors affecting the measurements, the degree of the effects, etc. These levels may be set so as to suit the target anti-cancer agent selected. The sensitivity determination may be performed as described above on the basis of the standards.

In the case where proteins A to D, F, H to K, and M are employed and 5-FU is a target anti-cancer agent, screening of an anti-cancer agent sensitivity enhancer can be performed through employment of variation in expression of any of the proteins, specifically suppression of the expression. That is, a substance which suppresses expression of protein in vitro or in vivo enhances sensitivity to an anti-cancer agent. For example, a substance which lowers protein levels in various cancer cells in the presence of an anti-cancer agent (in vitro) is a substance which enhances the sensitivity to the anti-cancer agent (i.e., anti-cancer agent sensitivity enhancer). Also, a substance which promotes lowering of protein levels in a cancer-bearing animal after administration of an anti-cancer agent (in vivo) is a substance which enhances the sensitivity to the anti-cancer agent (i.e., anti-cancer agent sensitivity enhancer). In the case where proteins A to D, G to K, and M are employed and L-OHP is a target anti-cancer agent, or in the case where proteins A to D, F, H to K, and M are employed and 5-FU/L-OHP combination is a target anti-cancer agent, screening of the anti-cancer agent sensitivity enhancer may be performed in the same manner as described above.

In the case where proteins E and G are employed and 5-FU/L-OHP combination is a target anti-cancer agent, screening of an anti-cancer agent sensitivity enhancer can be performed through employment of variation in expression of any of the proteins, specifically elevation of the expression. That is, a substance which elevates expression of protein in vitro or in vivo enhances sensitivity to an anti-cancer agent. For example, a substance which elevates protein levels in various cancer cells in the presence of an anti-cancer agent (in vitro) is a substance which enhances the sensitivity to the anti-cancer agent (i.e., anti-cancer agent sensitivity enhancer). Also, a substance which promotes elevation of protein levels in a cancer-bearing animal after administration of an anti-cancer agent (in vivo) is a substance which enhances the sensitivity to the anti-cancer agent (i.e., anti-cancer agent sensitivity enhancer).

In the case where proteins B, H, L, and N are employed and 5-FU, L-OHP, or 5-FU/L-OHP combination is a target anti-cancer agent, screening of an anti-cancer agent sensitivity enhancer can be performed through employment of variation in expression of any of the proteins, specifically elevation of the expression. That is, a substance which elevates expression of protein in vitro or in vivo enhances sensitivity to an anti-cancer agent. For example, a substance which elevates protein levels in various cancer cells in the absence of an anti-cancer agent (in vitro) is a substance which enhances the sensitivity to the anti-cancer agent (i.e., anti-cancer agent sensitivity enhancer). Also, a substance which promotes elevation of protein levels in a cancer-bearing animal before administration of an anti-cancer agent (in vivo) is a substance which enhances the sensitivity to the anti-cancer agent (i.e., anti-cancer agent sensitivity enhancer).

Through employment, in combination, of the thus-obtained anti-cancer agent sensitivity enhancer and an anti-cancer agent which is a sensitivity enhancement target of the enhancer, the therapeutic effect of the anti-cancer agent is drastically enhanced. The combination of the anti-cancer agent sensitivity enhancer and the anti-cancer agent which is a sensitivity enhancement target of the enhancer may be a composition containing both ingredients, or a combined drug of preparations containing individual ingredients. These two ingredients may be administered through different routes.

The target anti-cancer agents which may be employed here are the same as described above. Examples of the anti-cancer agent include oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, irinotecan, irinotecan active metabolite (SN-38), nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab/ozogamicin, bortezomib, erlotinib, cetuximab, bevacizumab, sunitinib, sorafenib, dasatinib, panitumumab, asparaginase, tretinoin, arsenic trioxide, salts thereof, and active metabolites thereof. Among them, fluoro-pyrimidine anti-cancer agents and platinum-based complex anti-cancer agents are preferred, with fluorouracil, oxaliplatin, and salts thereof being particularly preferred. It is preferably applied to a combination of fluorouracil or a salt thereof and oxaliplatin or a salt thereof.

EXAMPLES

The present invention will next be described in more detail by way of examples.

Example 1

(1) Method (a) Cells Employed

Two human colorectal cancer cell lines (HCT116 and DLD-1) were obtained from ECACC. Cell culturing was performed by means of a φ000 mm/Tissue Culture Dish (IWAKI) with a medium (D-MEM, 2 mM glutamine, 10% fetal bovine serum) at 37° C. under 5% $CO_2$.

(b) Drugs

Fluorouracil (5-FU) was purchased from Sigma, and oxaliplatin (L-OHP) powder was obtained from Kabushiki Kaisha Yakult Honsha.

(c) Evaluation of Sensitivity of Cancer to 5-FU, L-OHP, and a Combination of 5-FU and L-OHP (5-FU/L-OHP)

Two colorectal cancer cell lines (HCT116 and DLD-1) were exposed to a drug, and 24 hours and 48 hours after drug exposure, cell viability was determined by means of an MTS assay (CellTiter96™AQ$_{ueous}$ One Solution Cell Proliferation Assay, Promega). Drug exposure conditions were as follows. 5-FU (single agent) was used at the following 11 concentrations: control (0 μM), 0.001 μM, 0.01 μM, 0.1 μM, 1 μM, 3 μM, 10 μM, 30 μM, 100 μM, 1,000 μM, and 10,000 μM. L-OHP (single agent) was used at the following 11 concentrations; control (0 μM), 0.001 μM, 0.01 μM, 0.1 μM, 0.3 μM, 1 μM, 3 μM, 10 μM, 30 μM, 100 μM, and 1,000 μM. In the case of 5-FU/L-OHP combination, 5-FU was used at 2 μM, 10 μM, 30 μM, and 100 μM (4 concentrations), and L-OHP was used at 0.01 μM, 0.1 μM, 0.3 μM, 1 μM, 3 μM, 10 μM, 30 μM, 100 μM, and 1,000 μM (9 concentrations); i.e., 36 concentrations were employed. In addition, the above four 5-FU (single agent) concentrations, which were the same as employed in the case of 5-FU/L-OHP combination, and control (0 μM) were employed. Sensitivity evaluation was performed by use of three samples with respect to each cell line, drug exposure time, and drug exposure concentration in one experiment. The experiment was performed thrice by use of cells at different passage numbers.

Sensitivity analysis was performed from viability data calculated from MTS assay results. The presence or absence of combined effect was determined through comparison of viability obtained by exposure to a combination with that obtained by exposure to a single agent at the same concentration as employed at the exposure to the combination. When the viability obtained by exposure to a combination is significantly lowered as compared with each single agent case, the presence of a combination effect was confirmed.

(d) Drug Exposure Test

Based on the results of (c) above, the drug concentration employed in the exposure test was determined. The 5-FU+L-OHP combination concentration was adjusted to the following four levels: 2 μM+1 μM, 2 μM+10 μM, 100 μM+1 μM, and 100 μM+10 μM, the 5-FU concentration (exposure to single agent) was adjusted to 2 μM and 100 μM, and the L-OHP concentration (exposure to single agent) was adjusted to 1 μM and 10 μM. In addition, the exposure test was conducted at a drug-free concentration (control). That is, nine concentrations in total were employed. Drug exposure time was adjusted to the following five periods of time: 0 hour (just before exposure), 4 hours, 12 hours, 24 hours, and 48 hours. After completion of exposure, cell count was performed, and intracellular proteins were extracted.

(e) Extraction of Intracellular Proteins

The medium was removed from the dish and washed thrice with ice-cooled PBS. The cells on the dish was collected by scraping with a rubber policeman. The thus-obtained cell suspension was transferred to a 1.5-mL microtube. The cell suspension was centrifuged at 4° C. and 1,200×g for 10 minutes, and the cells were recovered. After removal of the supernatant, a cell lysis buffer (9 mol/L urea, 2% CHAPS, 1 mM DTT, protease-inhibitor cocktail (Sigma)) was added in a volume of 200 μL with respect to 10,000,000 cells. The liquid was subjected to untrasonic treatment under cooling with ice. The thus-treated product was centrifuged at 4° C. and 16,000×g for 20 minutes, and the supernatant was quickly frozen with liquid nitrogen. The frozen product was stored at −80° C. before analysis. An aliquot of the supernatant was subjected to protein quantification (DC Protein Assay Kit, Bio-Rad).

(f) Preparation of Samples for Protein Expression Analysis with Proteinchip and Expression Analysis of Intracellular Proteins The protein sample was mixed with a cell lysis buffer (excluding protease inhibitor), to thereby adjust the protein concentration to 2.5 mg/mL. The liquid was further mixed with a dilution/washing buffer (pH: 4.5, 50 mM sodium acetate buffer) (hereinafter referred to simply as "buffer"), to a protein concentration of 0.5 mg/mL. The thus-prepared sample (100 μL) was applied to spots of a cation-exchange ProteinChip array (CM10, Bio-Rad) which had been conditioned in advance with the same buffer. Incubation was performed for one hour for reaction, and the chip array was washed thrice with the buffer and rinsed twice with milliQ water, followed by drying in air. Energy absorbing molecule (EAM: saturated solution of sinapinic acid in 50% ACN/0.5% TFA) (1.0 μL (0.5 mL×2)) was added to each spot. After the surface of the spot was dried, analysis of the ProteinChip array was performed.

Protein expression analysis was performed through surface-enhanced laser desorption/ionization time-of-flight mass spectrometry (SELDI-TOF MS). As an analyzer, ProteinChip™ Reader (Model PCS4000 Personal Edition, Bio-Rad) was used and the analysis was performed under the following conditions: mass range of 0 to 70,000 Da, focus mass of 8,000 Da, energy of 3,000 or 4,000 nJ, and 265 shots/sample. Peak extraction (signal-to-noise ratio (S/N)≥2) and protein expression comparative analysis were performed by means of CiphergenExpress™ Data Manager 3.0.

(g) Selection of Candidate Peaks

Through SELDI-TOF MS analysis, 88 to 143 protein peaks were selected from each sample (S/N≥2). Firstly, a peak cluster was made by means of CiphergenExpress™ Data Manager 3.0. Then, under tested conditions, there were selected peaks exhibiting a significant change in intensity over time after exposure to a drug, and peaks exhibiting significantly different intensities depending on the selected drug at exposure times (4, 12, 24, and 48 hours). Then, peaks overlapping the above two conditions; i.e., peaks exhibiting variation in expression due to exposure time and depending on the type of the drug, were selected.

(2) Results (a) Evaluation of Drug Sensitivity of HCT116 and DLD-1

The cell viabilities after exposure to 100 μM 5-FU for 48 hours were about 24% (HCT116) and about 49% (DLD-1). Thus, DLD-1 was found to have sensitivity to 5-FU lower than that of HCT116. The cell viabilities after exposure to 1 μM L-OHP for 48 hours were about 37% (HCT116) and about 82% (DLD-1). Thus, DLD-1 was found to have sensitivity to L-OHP lower than that of HCT116. Regarding 5-FU/L-OHP combination, HCT116 exhibited significantly lower cell viabilities after exposure to 2 μM 5-FU+1 μM L-OHP for 24 hours and 100 μM 5-FU+10 μM L-OHP for 48 hours, as compared with the cases where corresponding single agents were used, indicating a combination effect. However, DLD-1 exhibited no significant combination effect. Therefore, HCT116 was found to have high sensitivity to 5-FU/L-OHP combination, and DLD-1 was found to have low sensitivity to 5-FU/L-OHP combination (FIG. 1).

(b) Protein Expression Analysis

Through proteome analysis employing SELDI-TOF MS, variation in intracellular protein level associated with exposure to 5-FU, L-OHP, or 5-FU/L-OHP combination was comprehensively analyzed. The analysis was performed through a technique as described in (1) above. As a result, the following proteins exhibiting characteristic level variations after exposure to the drugs were selected.

(5-FU)

As a result of analysis of intracellular protein level time-dependent profile after exposure to 5-FU, the followings were observed.

(1) Peaks exhibiting, after exposure to 5-FU, a protein level increase only in DLD-1, or a protein level increase larger in DLD-1 than in HCT116 (FIG. 2, FIG. 3, FIG. 4(a), FIG. 7(a), FIG. 9, FIG. 10, FIG. 11(a), and FIG. 12)

m/z of 5,300 to 5,400 (protein A)
m/z of 6,130 to 6,230 (protein B)
m/z of 7,000 to 7,080 (protein C)
m/z of 11,020 to 11,120 (protein F)
m/z of 17,100 to 17,270 (protein H)
m/z of 18,290 to 18,470 (protein I)
m/z of 24,660 to 24,750 (protein J)
m/z of 35,980 to 36,290 (protein K)

Figure 5:
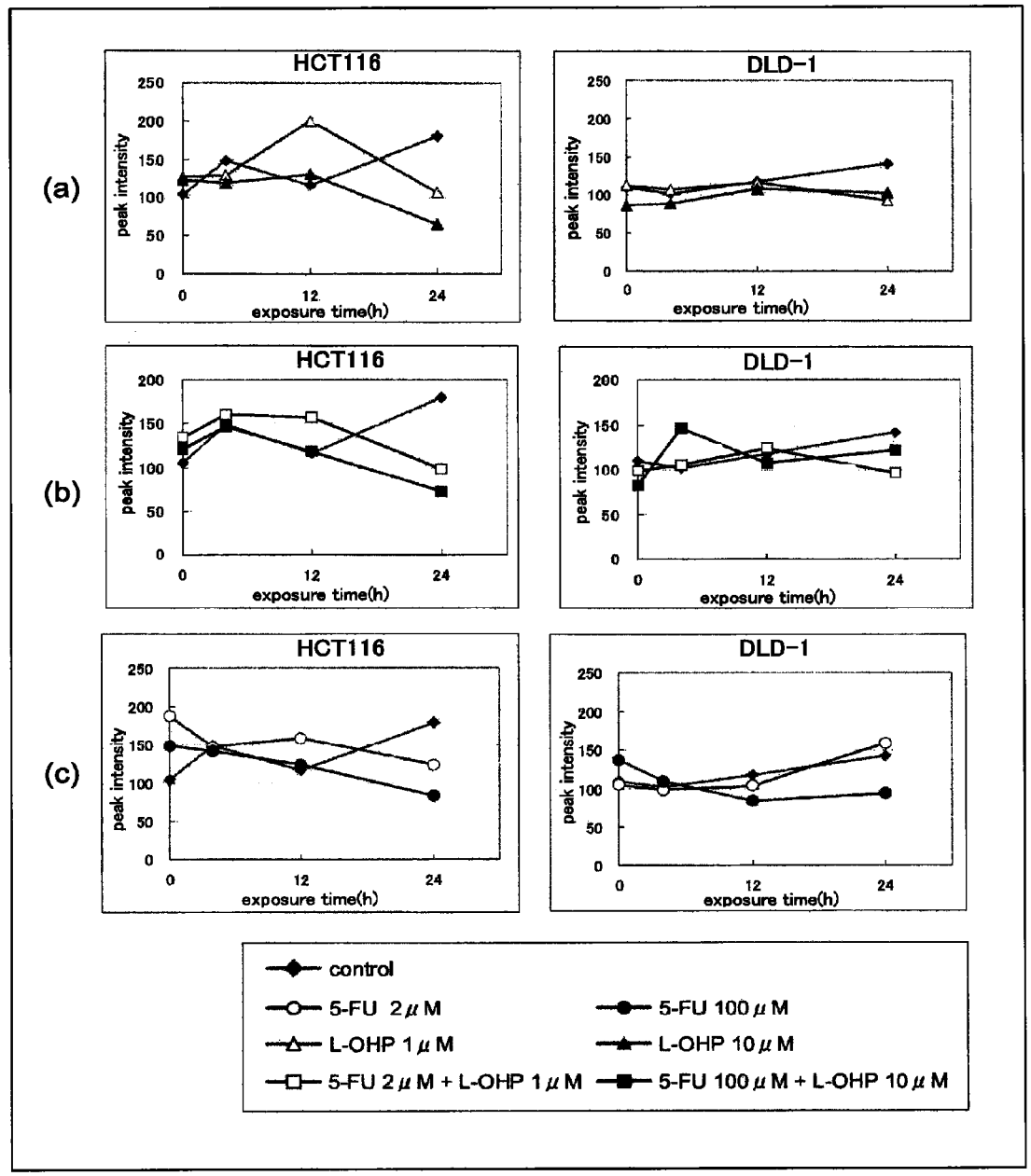
FIG. 5 Graphs showing a time-dependent profile of the intracellular protein D level in HCT116 cells after exposure to 5-FU, L-OHP, or 5-FU/L-OHP, and graphs showing a time-dependent profile of the intracellular protein D level in DLD-1 cells after exposure to 5-FU, L-OHP, or 5-FU/L-OHP.
Figure 14:
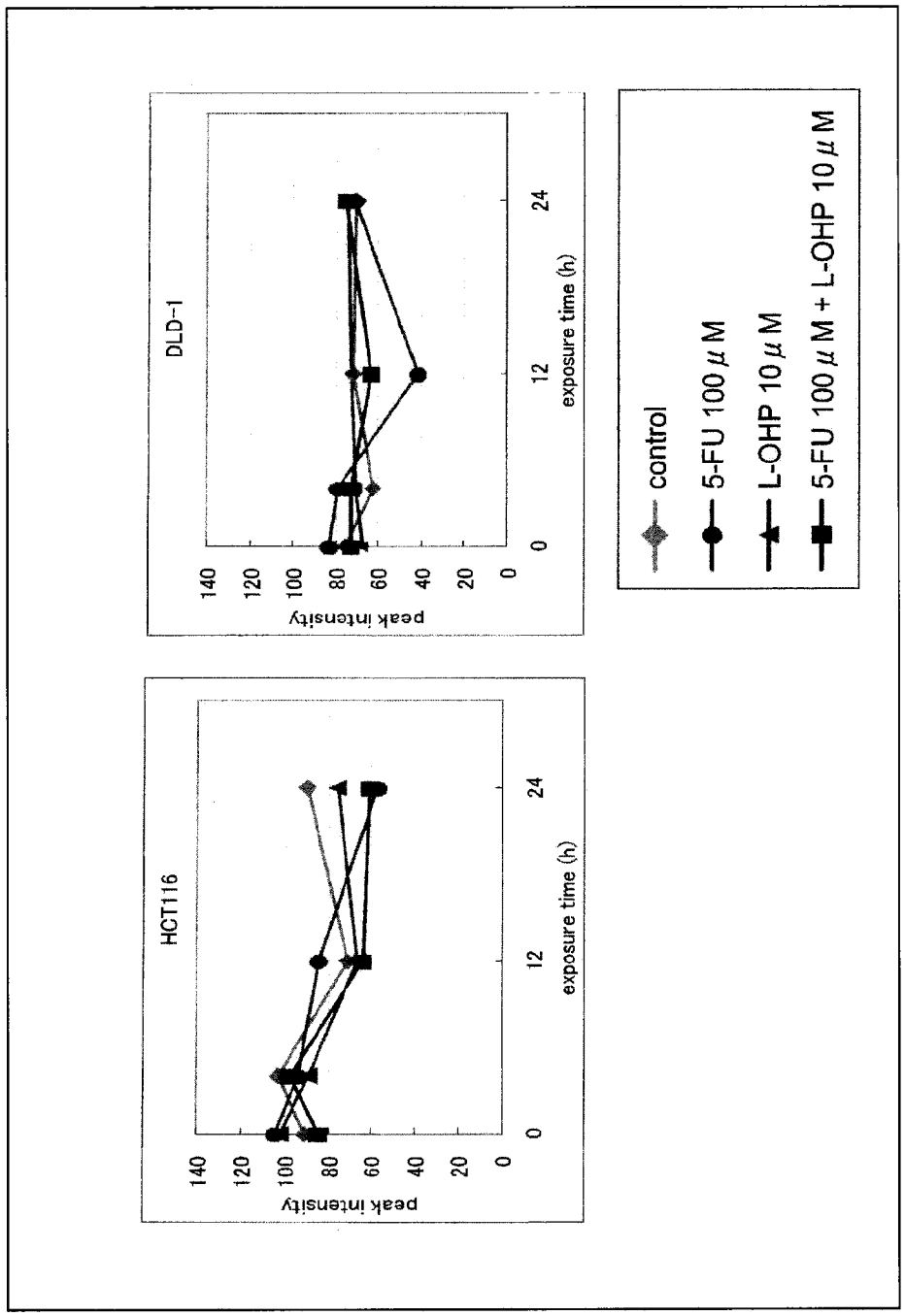
FIG. 14 A graph showing a time-dependent profile of the intracellular protein M level in HCT116 cells after exposure to 5-FU, L-OHP, or 5-FU/L-OHP, and a graph showing a time-dependent profile of the intracellular protein M level in DLD-1 cells after exposure to 5-FU, L-OHP, or 5-FU/L-OHP.

(2) Peaks exhibiting, after exposure to 5-FU, a protein level decrease in HCT116 (FIG. 5(c) and FIG. 14)

m/z of 7,840 to 7,920 (protein D)
m/z of 9,100 to 9,200 (protein M)

(L-OHP)

As a result of analysis of intracellular protein level time-dependent profile after exposure to L-OHP, the followings were observed.

(1) Peaks exhibiting, after exposure to L-OHP, a protein level increase only in DLD-1, or a protein level increase larger in DLD-1 than in HCT116 (FIG. 2, FIG. 3, FIG. 4(b), FIG. 7(b), FIG. 8(a), FIG. 9, FIG. 10, FIG. 11(c), and FIG. 12)

m/z of 5,300 to 5,400 (protein A)
m/z of 6,130 to 6,230 (protein B)
m/z of 7,000 to 7,080 (protein C)
m/z of 11,020 to 11,120 (protein F)
m/z of 12,440 to 12,560 (protein G)
m/z of 17,100 to 17,270 (protein H)
m/z of 18,290 to 18,470 (protein I)
m/z of 24,660 to 24,750 (protein J)
m/z of 35,980 to 36,290 (protein K)

(2) Peaks exhibiting, after exposure to L-OHP, a protein level decrease in HCT116 (FIG. 5(a) and FIG. 14)

m/z of 7,840 to 7,920 (protein D)
m/z of 9,100 to 9,200 (protein M)

(5-FU/L-OHP)

As a result of analysis of intracellular protein level time-dependent profile after exposure to 5-FU/L-OHP combination, the followings were observed.

(1) Peaks exhibiting, after exposure to 5-FU/L-OHP combination, a protein level increase only in DLD-1, or a protein level increase larger in DLD-1 than in HCT116 (FIG. 2, FIG. 3, FIG. 4(c), FIG. 7(c), FIG. 9, FIG. 10, FIG. 11(b), and FIG. 12)

m/z of 5,300 to 5,400 (protein A)
m/z of 6,130 to 6,230 (protein B)
m/z of 7,000 to 7,080 (protein C)
m/z of 11,020 to 11,120 (protein F)
m/z of 17,100 to 17,270 (protein H)
m/z of 18,290 to 18,470 (protein I)
m/z of 24,660 to 24,750 (protein J)
m/z of 35,980 to 36,290 (protein K)

Figure 6:
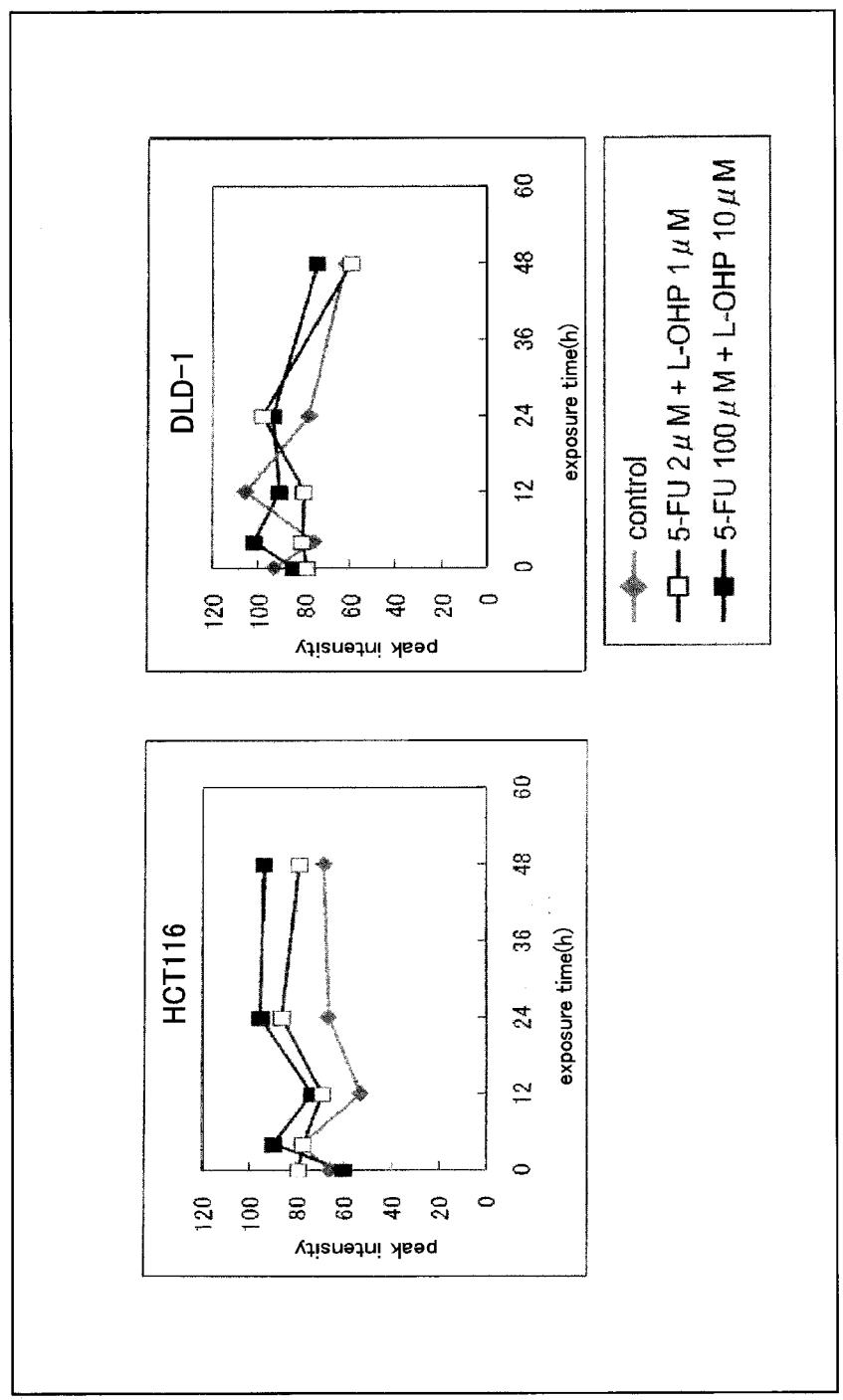
FIG. 6 A graph showing a time-dependent profile of the intracellular protein E level in HCT116 cells after exposure to 5-FU/L-OHP, and a graph showing a time-dependent profile of the intracellular protein E level in DLD-1 cells after exposure to 5-FU/L-OHP.
Figure 7:
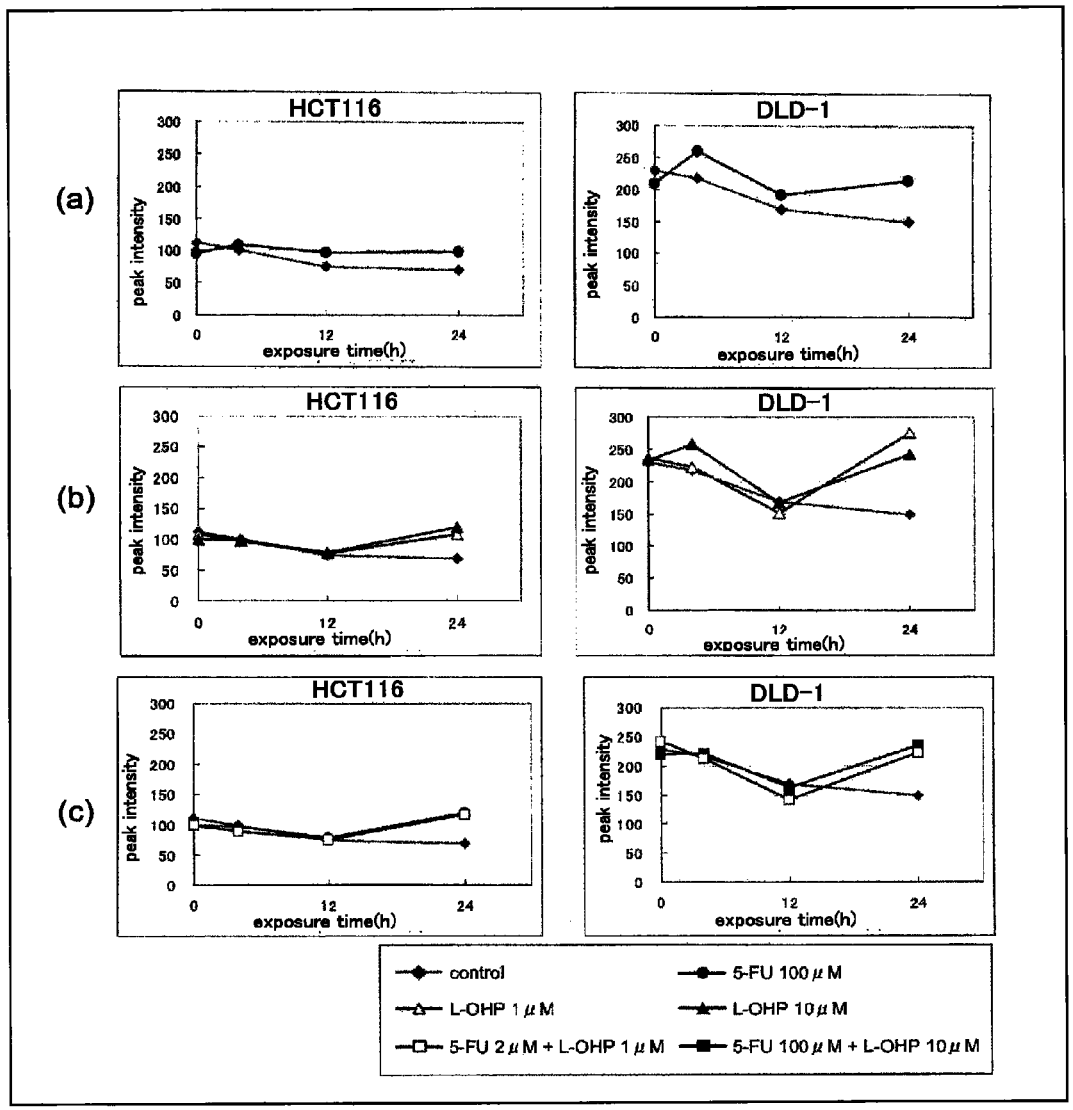
FIG. 7 Graphs showing a time-dependent profile of the intracellular protein F level in HCT116 cells after exposure to 5-FU, L-OHP, or 5-FU/L-OHP, and graphs showing a time-dependent profile of the intracellular protein F level in DLD-1 cells after exposure to 5-FU, L-OHP, or 5-FU/L-OHP.
Figure 8:
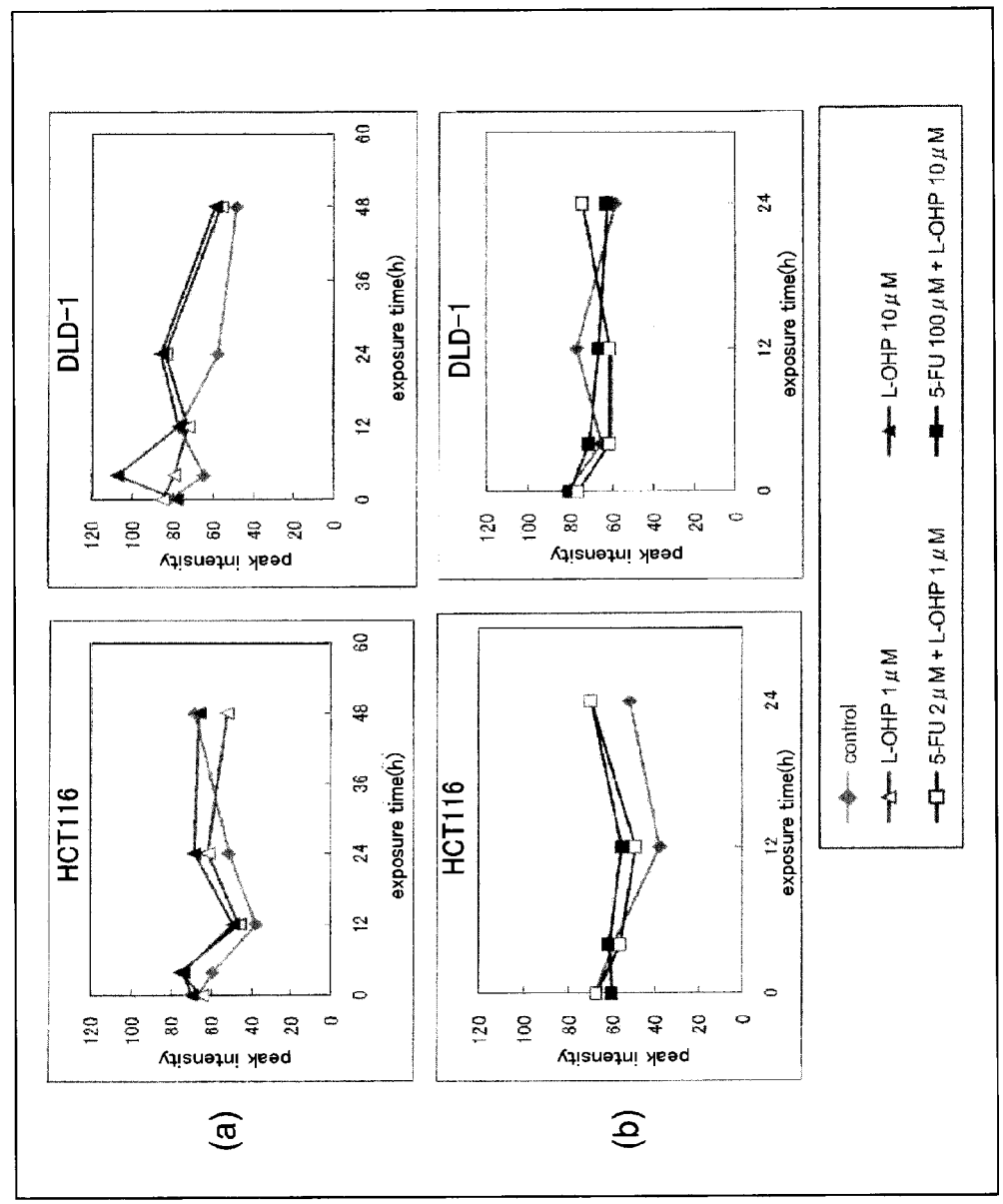
FIG. 8 Graphs showing a time-dependent profile of the intracellular protein G level in HCT116 cells after exposure to L-OHP or 5-FU/L-OHP, and graphs showing a time-dependent profile of the intracellular protein G level in DLD-1 cells after exposure to L-OHP or 5-FU/L-OHP.
Figure 9:
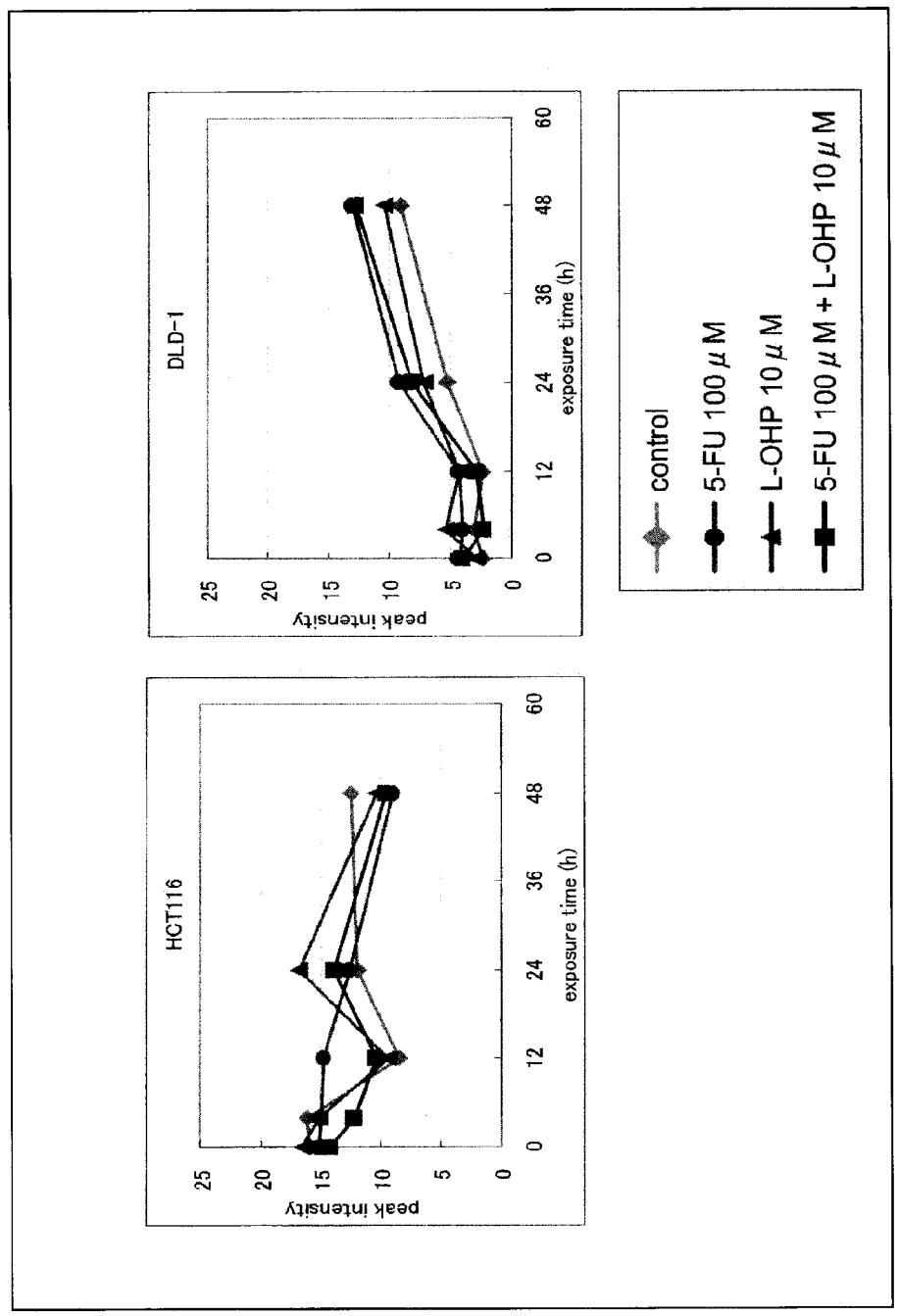
FIG. 9 A graph showing a time-dependent profile of the intracellular protein H level in HCT116 cells after exposure to 5-FU, L-OHP, or 5-FU/L-OHP, and a graph showing a time-dependent profile of the intracellular protein H level in DLD-1 cells after exposure to 5-FU, L-OHP, or 5-FU/L-OHP.
Figure 10:
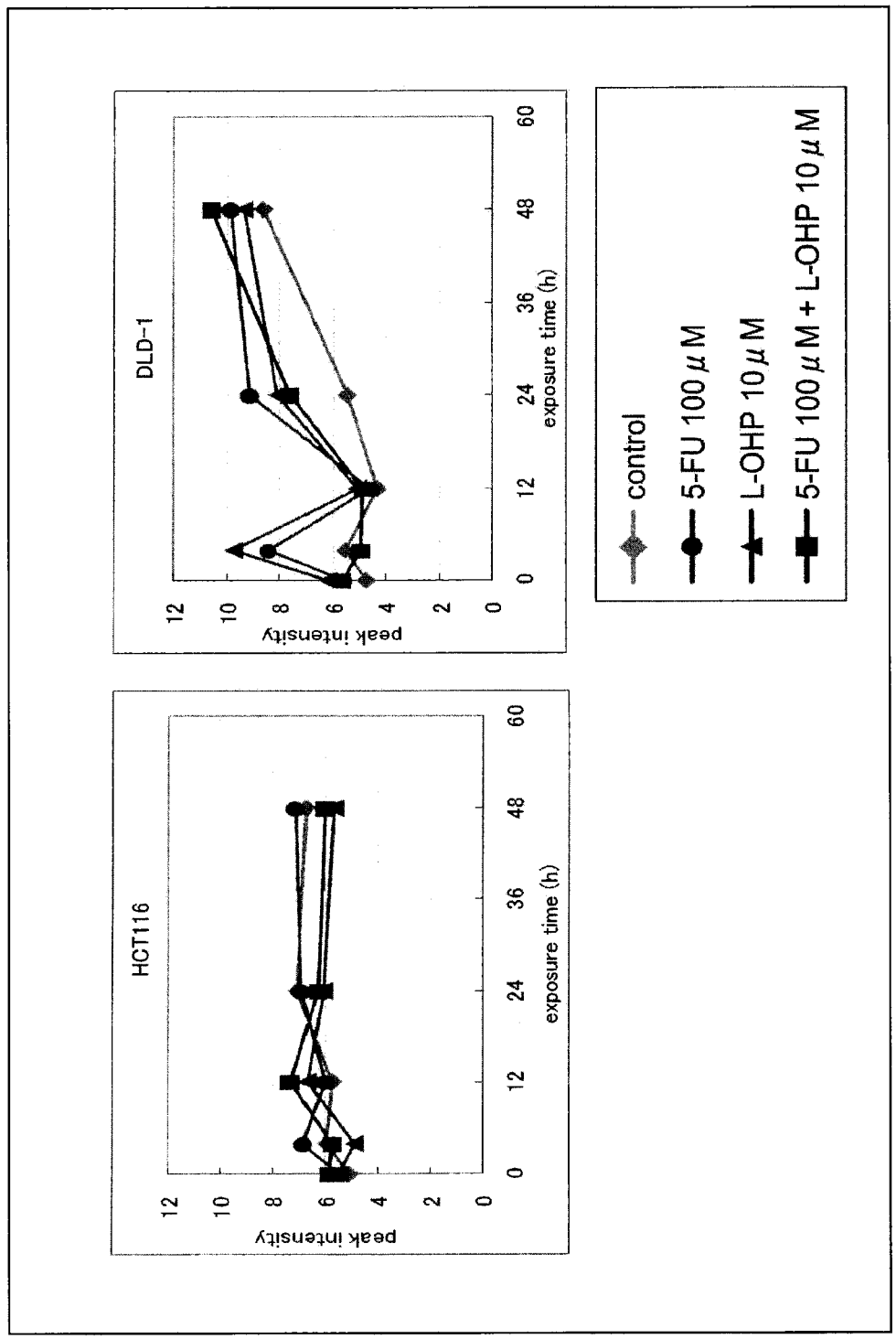
FIG. 10 A graph showing a time-dependent profile of the intracellular protein I level in HCT116 cells after exposure to 5-FU, L-OHP, or 5-FU/L-OHP, and a graph showing a time-dependent profile of the intracellular protein I level in DLD-1 cells after exposure to 5-FU, L-OHP, or 5-FU/L-OHP.
Figure 11:
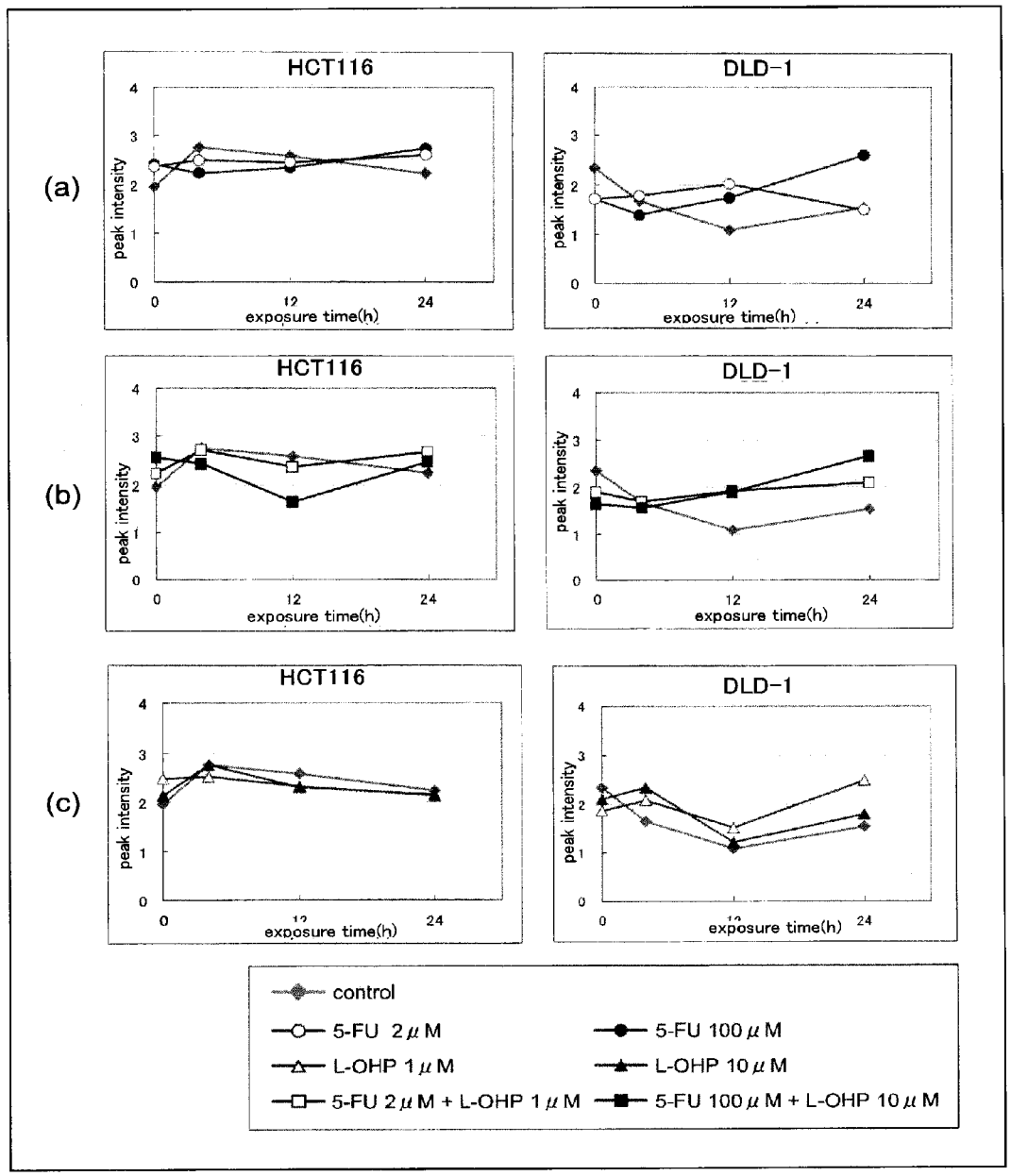
FIG. 11 Graphs showing a time-dependent profile of the intracellular protein J level in HCT116 cells after exposure to 5-FU, L-OHP, or 5-FU/L-OHP, and graphs showing a time-dependent profile of the intracellular protein J level in DLD-1 cells after exposure to 5-FU, L-OHP, or 5-FU/L-OHP.
Figure 12:
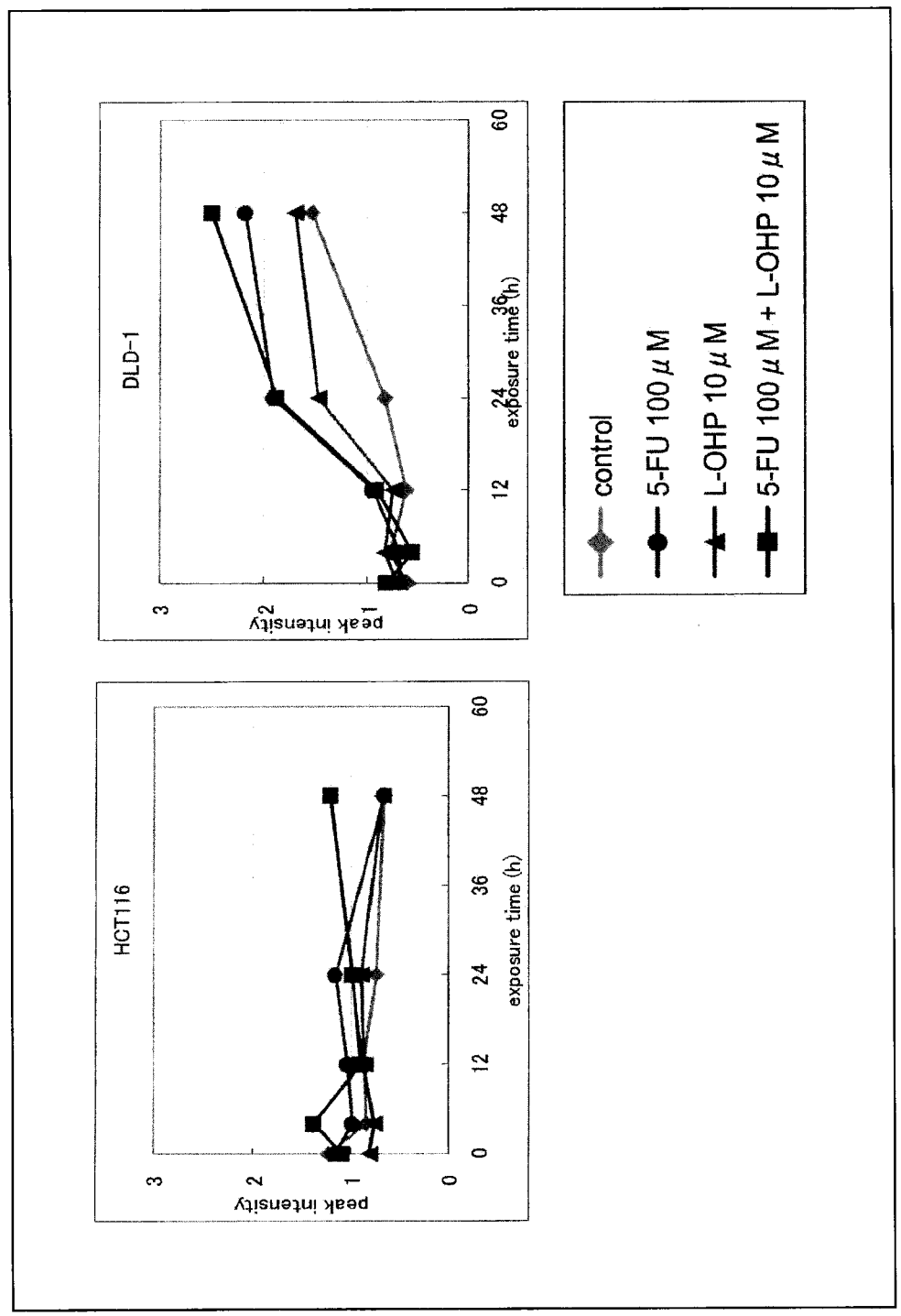
FIG. 12 A graph showing a time-dependent profile of the intracellular protein K level in HCT116 cells after exposure to 5-FU, L-OHP, or 5-FU/L-OHP, and a graph showing a time-dependent profile of the intracellular protein K level in DLD-1 cells after exposure to 5-FU, L-OHP, or 5-FU/L-OHP.

(2) Peaks exhibiting, after exposure to 5-FU/L-OHP combination, a protein level increase in HCT116 (FIG. 6 and FIG. 8(b))

m/z of 8,920 to 9,000 (protein E)
m/z of 12,440 to 12,560 (protein G)

(3) Peaks exhibiting, after exposure to 5-FU/L-OHP, a protein level decrease in HCT116 (FIG. 5(b) and FIG. 14)

m/z of 7,840 to 7,920 (protein D)
m/z of 9,100 to 9,200 (protein M)

(Intracellular protein level before exposure to drug) Peaks exhibiting, before drug exposure (not exposed), a protein level significantly higher in HCT116 than in DLD-1 m/z of 6,130 to 6,230 (protein B)
m/z of 8,650 to 8,750 (protein L)
m/z of 11,760 to 11,890 (protein N)
m/z of 17,100 to 17,270 (protein H)

Intracellular protein B levels before drug exposure, represented by a peak intensity obtained by SELDI-TOF MS analysis (μA) (av. ±S.D., n=27), were 55.4±9.2 (HCT116) and 28.9±6.4 (DLD-1). Similarly, intracellular protein L levels were 88.2±2.2 (HCT116) and 32.1±1.3 (DLD-1), protein N levels 85.1±9.3 (HCT116) and 50.6±6.0 (DLD-1), and protein H levels 15.5±2.1 (HCT116) and 3.86±1.34 (DLD-1). Thus, these proteins exhibited an intracellular level significantly higher in HCT116 than in DLD-1, before drug exposure (not exposed).

Example 2

All the peaks (m/z) detected in Example 1 were confirmed through internal molecular weight calibration by use of two molecular weight standards sandwiching a target peak. The following standard substances having a known molecular weight were employed: insulin oxidized B chain (bovine) (m/z: 3496.94+1H), insulin (bovine) (m/z: 5733.51+1H), cytochrome c (equine) (m/z: 12360.96+1H), apomyoglobin (equine) (m/z: 16952.27+1H), and aldorase (rabbit muscle) (m/z: 39212.28+1H). As a result, the peaks of Example 1 were found to be detected at an m/z of 5,300 to 5,400 (protein A), an m/z of 6,130 to 6,230 (protein B), an m/z of 7,000 to 7,080 (protein C), an m/z of 7,840 to 7,920 (protein D), an m/z of 8,920 to 9,000 (protein E), an m/z of 11,020 to 11,120 (protein F), an m/z of 12,440 to 12,560 (protein G), an m/z of 17,100 to 17,270 (protein H), an m/z of 18,290 to 18,470 (protein I), an m/z of 24,660 to 24,750 (protein J), an m/z of 35,980 to 36,290 (protein K), an m/z of 8,650 to 8,750 (protein L), an m/z of 9,100 to 9,200 (protein M), and an m/z of 11,760 to 11,890 (protein N).

Example 3

The features of the peaks found in Example 1 were further investigated in terms of variation in peak intensity associated with change in pH.

(1) Method (a) Proteinchip Array and Buffer Conditions Employed in the Study

For a cation-exchange ProteinChip array (CM10, Bio-Rad), the following 15 types of buffers were used: pH: 3.0 (50 mM glycine-HCl buffer), pH: 3.5 (50 mM sodium acetate buffer), pH: 4.0 (50 mM sodium acetate buffer), pH: 4.5 (50 mM sodium acetate buffer), pH: 5.0 (50 mM sodium acetate buffer), pH: 5.5 (50 mM sodium acetate buffer), pH: 6.0 (50 mM phosphate buffer), pH: 6.5 (50 mM phosphate buffer), pH: 7.0 (50 mM phosphate buffer), pH: 7.5 (50 mM phosphate buffer), pH: 8.0 (50 mM Tris-HCl buffer), pH: 8.5 (50 mM Tris-HCl buffer), pH: 9.0 (50 mM glycine-NaOH buffer), pH: 9.5 (50 mM glycine-NaOH buffer), and pH: 10.0 (50 mM glycine-NaOH buffer).

(b) Preparation of Samples for CM10 Chip Array Analysis and Analysis Conditions

Preparation of samples for CM10 chip array analysis, and production of protein chips were performed by use of buffers of (a) in accordance with (f) of method (1) of Example 1.

(2) Results

In the CM10 chip array analysis, the pH at which the relevant peak intensity drops is thought to be the isoelectric point (pI) of the protein, where an ionized form is neutralized. As a result, the peaks detected in Example 1 were found to have the following estimated isoelectric points (pIs):

a pH of 3.5 to 6.5 (m/z of 7,000 to 7,080 (protein C)),
a pH of 4.0 to 7.0 (m/z of 8,920 to 9,000 (protein E)),
a pH of 7.0 to 8.0 (m/z of 11,020 to 11,120 (protein F)),
a pH of 4.5 to 7.5 (m/z of 12,440 to 12,560 (protein G)),
a pH of 5.0 to 8.0 (m/z of 17,100 to 17,270 (protein H)),
a pH of 6.5 to 9.5 (m/z of 18,290 to 18,470 (protein I)),
a pH of 3.5 to 6.5 (m/z of 24,660 to 24,750 (protein J)),
a pH of 3.0 to 6.5 (m/z of 35,980 to 36,290 (protein K)),
a pH of 4.5 to 7.0 (m/z of 8,650 to 8,750 (protein L)),
a pH of 4.5 to 7.5 (m/z of 9,100 to 9,200 (protein M)), and
a pH of 4.5 to 7.5 (m/z of 11,760 to 11,890 (protein N)).

Regarding protein A (m/z of 5,300 to 5,400) protein B (m/z of 6,130 to 6,230), and protein D (m/z of 7,840 to 7,920), the pH at which the peak drop occurred was not definitely detected.

Example 4

Based on the results of Examples 2 and 3, the peaks detected in Example 1 were subjected to database searching by use of TagIdent tool (http://au.expasy.org/tools/tagident.html) of The ExPASy proteomics server. The results are as follows.

TABLE 1

| Proteins or fragments thereof detected | Results of retrieval Protein name (UniProtKB/Swiss-Prot Accession number) |
|---|---|
| m/z 5,300~ 5,400 (protein A) | Putative inactivation escape 1 protein. (O15225), Cytochrome coxidase subunit 7C, mitochondrial. (P15954), Beta-defensin 134. (Q4QY38), Putative spermatogenes is - related protein 7. (Q6W4Z2), Oculomedin. (Q9Y5M6) |
| m/z 6,130~ 6,230 (protein B) | Epidermal growth factor. (P01133). Metallothionein-1A. (P04731), Metallothionein-1G. (P13640), 60 S ribosomal protein L40. (P62987), Beta-defensin 135. (Q30KP9), Keratin-associated protein 20-1. (Q3LI63), Putative 60 S ribosomal protein L39-like 5. (Q59GN2), 60 S ribosomal protein L-39 like. (Q96EH5), Uncharacterized protein C9 or f70. (Q96IN3), Putataive uncharacterized protein PRO1617. (Q9P1J0), Uncharacterized protein C6 or f123. (Q9Y6Z2) |
| m/z 7,000~ 7,080 (protein C) | Guanine nucleotide-binding protein G (I)/G (S)/G (O) subunit gamma-7. (O60262), Neutrophil-activating peptide 2 (1-63). (P02775), CCB peptide. (P05060), DNA-directed RNA polymerases I, II, and III subunit RPABC4. (P53803), Uncharacterized protein C21 orf90. (P59090), Putative uncharacterized protein C1orf134. (Q5TEV5), Putative uncharacterized prote in LOC550643. (Q63Z42), Putative uncharacterized protein SNHG12. (Q9BXW3), Coiled-coil domain-containing protein 72. (Q9Y2S6) |

TABLE 2

| Proteins or fragments thereof detected | Results of retrieval Protein name (UniProtKB/Swiss-Prot Accession number) |
|---|---|
| m/z 7,840 to 7,920 (protein D) | Putative uncharacterized protein C9orf118. (A6NHY6), Progonadoliberin-1. (P01148), Growth-regulated alpha protein.(P09341), Platelet factor 4 variant(4-74). (P10720), Uteroglobin. (P11684),C-C motif chemokine 5. (P13501), C-X-C motif chemokine 2. (P19875), C-X-C motif chemokine 3. (P19876), Small proline-rich protein 2E. (P22531),Small proline-rich protein 2D. (P22532),C-C motif chemokine 18. (P55774),cAMP-dependent protein kinase inhibitor alpha. (P61925), 40S ribosomal protein S28. (P62857), Small-inducible cytokine B6,N-processed variant 2. (P80162), Protein FAM7A. (QOP5Q8), Adipose most abundant gene transcript 2 protein. (Q15847), Neuronal protein 3.1. (Q16612), Putative uncharacterized protein LOC100133313. (Q5VUR6), Uncharacterized protein C9orf165. (Q6UWT2), Otospiralin. (Q8NHW6), Secretoglobin family 3A member 2. (Q96PL1), Putative transcript Y 9 protein. (Q9BZA1), Augurin. (Q9H1Z8), Uncharacterized protein C9orf27. (Q9P2X8), Putative uncharacterized protein L0051152. (Q9UMX8), cAMP-dependent protein kinase inhibitor gamma. (Q9Y2B9) |

TABLE 3

| Proteins or fragments thereof detected | Results of retrieval Protein name (UniProtKB/Swiss-Prot Accession number) |
|---|---|
| m/z 8,920 to 9,000 (protein E) | Stimulated by retinoic acid gene 13 protein homolog. (A8MT69), Leukemia-associated protein 1. (O43261), GnRH-associated peptide 2. (O43555), Scrapie-responsive protein 1. (O75711), Activation peptide. (P00747), Apolipoprotein C-II. (P02655), Saposin-B-Val. (P07602), Cortexin-2. (POC2S0), Interleukin-8. (P10145), CD59 glycoprotein. (P13987), ATP synthase-coupling factor 6, mitochondrial. (P18859), Betacellulin. (P35070), Secreted Ly-6/uPAR-related protein 1. (P55000), CCL23(22-99). (P55773), HERV-K3q12.3 provirus Np9 protein. (P61583), Ubiquitin-fold modifier 1. (P61960), C-C motif chemokine 8. (P80075), C-C motif chemokine 7. (P80098), Putative uncharacterized protein LOC440356. (Q0VD67), Putative uncharacterized protein C21orf49. (Q17RA5), Cortexin-3. (Q4LDR2), MORNrepeat-containing protein 2. (Q502X0),Putative Rho GTPase-activating protein 27-like protein. (Q66K37), Putative protein RNF216-like. (Q6NUR6), Keratin-associated protein 19-1. (Q8IUB9), Musculoskeletal embryonic nuclear protein 1. (Q8IVN3), CDC42 small effector protein 1. (Q9NRR8), Kidney-associated antigen 1. (Q9UBP8), Immediate early response 3-interacting protein 1. (Q9Y5U9) |

TABLE 4

| Proteins or fragments thereof detected | Results of retrieval Protein name (UniProtKB/Swiss-Prot Accession number) |
|---|---|
| m/z 11,020 to 11,120 (protein F) | Protein S100-A10. (P60903) |
| m/z 12,440 to 12,560 (protein G) | Transmembrane protein 218. (A2RU14),Transmembrane protein 210. (A6NLX4), Agouti-related protein. (O00253), |

TABLE 4-continued

| Proteins or fragments thereof detected | Results of retrieval Protein name (UniProtKB/Swiss-Prot Accession number) |
|---|---|
| | Growth/differentiation factor 11. (O95390), Follitropin subunit beta. (P01225), Cytochrome c oxidase subunit 5A, mitochondrial. (P20674), Inhibin beta C chain. (P55103), Vesicle-associated membrane protein 2. (P63027), Dynein light chain Tctex-type 1. (P63172), Eukaryotic translation initiation factor 4E-binding protein 1. (Q13541), Transcription elongation factor B polypeptide 1. (Q15369), Apolipoprotein(a)-like protein 2. (Q16609), Putative G antigen family D member 1. (Q5JUK9), UPF0545 protein C22orf39. (Q6P5X5), Notch-regulated ankyrin repeat-containing protein. (Q7Z6K4), Coiled-coil-helix-coiled-coil-helix domain-containing protein 10, mitochondrial. (Q8WYQ3), Growth/differentiation factor 15. (Q99988), Otoraplin. (Q9NRC9), Placenta-specific gene 8 protein. (Q9NZF1), Ig heavy chain V-I region EU. (P01742), Transcription initiation factor IIA subunit 2. (P52657), UPF0258 protein KIAA1024-like. (P59773), Uncharacterized protein C2orf14-like 2. (A8MVP8), Ig heavy chain V-III region TEI. (P01777), Thy-1 membrane glycoprotein. (P04216), 60 S ribosomal protein L35a. (P18077), Transcription factor BTF3 homolog 1. (Q13890), COX assembly mitochondrial protein homolog. (Q7Z7K0), Putative uncharacterized protein C19orf49. (Q86XP5), Uncharacterized protein C16orf52. (Q8NHV5) |

TABLE 5a

| Proteins or fragments thereof detected | Results of retrieval Protein name (UniProtKB/Swiss-Prot Accession number) |
|---|---|
| m/z 17,100 to 17,270 (protein H) | Oocyte-expressed protein homolog. (A6NGQ2), Putative calcium-activated potassium channel subunit beta-3-like protein. (A8MYL6), Heat shock protein beta-6. (O14558), HERV-K_5q33.3 provirus ancestral Pro protein. (P10265), Nucleoside diphosphate kinase A. (P15531), Stathmin. (P16949), Interleukin-1 receptor antagonist protein. (P18510), 3-hydroxyanthranilate 3,4-dioxygenase. (P46952-2), Glycoprotein Xg. (P55808), Caveolin-3. (P56539), Ubiquitin-conjugating enzyme E2 N. (P61088), Protein mago nashi homolog. (P61326), HERV-K_12q14.1 provirus ancestral Pro protein. (P63119), HERV-K_19q12 provirus ancestral Pro protein. (P63120), HERV-K_19p13.11 provirus ancestral Pro protein. (P63121), HERV-K_1q23.3 provirus ancestral Pro protein. (P63123), HERV-K_5q13.3 provirus ancestral Pro protein. (P63124), HERV-K_22q11.21 provirus ancestral Pro protein. (P63129), Microfibrillar-associated protein 5. (Q13361), Protein CROC-4. (Q13536), Frataxin(56-210). (Q16595), Protein FAM182A. (Q5T1J6), Putative uncharacterized protein FLJ42147. (Q6ZVS6), Uncharacterized protein C14orf65. (Q8N9R9), Protein mago nashi homolog 2. (Q96A72), Uncharacterized protein UNQ773/PRO1567. (Q96DA0), FXYD domain-containingion transport regulator 5. (Q96DB9), |

TABLE 5b

| Proteins or fragments thereof detected | Results of retrieval Protein name (UniProtKB/Swiss-Prot Accession number) |
|---|---|
| m/z 17,100 to 17,270 (protein H) | Transcription factor BTF3 homolog 4. (Q96K17), Lipopolysaccharide-induced tumor necrosis factor-alpha factor. (Q99732), Complexin-3. (Q8WVH0), Nucleoside diphosphate kinase, mitochondrial. (O00746), Tumor necrosis factor ligand superfamily member 12. (O43508), Cytochrome c oxidase subunit 4 isoform 1, mitochondrial. (P13073), HERV-K_8p23.1 provirus ancestral Pro protein. (P63122), HERV-K_6q14.1 provirus ancestral Pro protein. (P63127), Putative RNA-binding protein 3. (P98179), Putative RRN3-like protein FLJ77916. (Q2M238), Protein ZNF767. (Q75MW2), FUN14 domain-containing protein 1. (Q8IVP5), Putative uncharacterized protein C20orf78. (Q9BR46), Transmembrane protein C9orf46. (Q9HBL7), H/ACA ribonucleoprotein complex subunit 2. (Q9NX24), Chemokine-like factor. (Q9UBR5), RING finger protein 24. (Q9Y225), Uncharacterized protein C5orf50. (A6NLE4), ATP synthase subunit d, mitochondrial. (O75947), HERV-K_1p13.3 provirus ancestral Gag polyprotein. (P62686), Troponin C, slow skeletal and cardiac muscles. (P63316), UPF0484 protein FAM167B. (Q9BTA0), Protein FAM176B. (Q9NVM1), Uncharacterized protein LOC389203. (Q8N5G0), Putative uncharacterized protein C12orf33. (Q8N6U2) |

TABLE 6

| Proteins or fragments thereof detected | Results of retrieval Protein name (UniProtKB/Swiss-Prot Accession number) |
|---|---|
| m/z 18,290 to 18,470 (protein I) | Putative ankyrin repeat domain-containing protein 20A5(A0PJZ0), Probable ubiquitin-conjugating enzyme E2 FLJ25076. (A1L167), UPF0627 protein ENSP00000341061/ENSP00000339743. (A6NEA5), Putative protein FAM86C-like 2. (A6NEL3), Uncharacterized protein C15orf62, mitochondrial. (A8K5M9), Uncharacterized protein C16orf90. (A8MZG2), Ubiquitin D. (O15205), Mitochondrial import inner membrane translocase subunit Tim17-B. (O60830), Interleukin-18-binding protein. (O95998), Erythropoietin. (P01588), Cofilin-1. (P23528), Rhombotin-2. (P25791), Translocon-associated protein subunit beta. (P43308), membrane protein 3. (P54852), Tubulin polymerization-promoting protein family member 2. (P59282), Destrin. (P60981), Putative survival-related protein. (Q2EN02), Dual specificity phosphatase 28. (Q4G0W2), UPF0627 protein ENSP00000358171. (Q6ZW35), Gastrokine-2. (Q86XP6),Keratin-associated protein 13-1. (Q8IUCO), Putative uncharacterized protein CXorf62. (Q8N2A0), 39S ribosomal protein L50, mitochondrial. (Q8N5N7), Bcl2 antagonist of cell death. (Q92934), Uncharacterized protein C19orf43. (Q9BQ61), Keratin-associated protein 9-2. (Q9BYQ4), Williams-Beuren syndrome chromosomal region 23 protein. (Q9H6D5), Transmembrane protein (By similarity). (Q9N2J8),Protein FAM86C. (Q9NVL1) |

TABLE 7

| Proteins or fragments thereof detected | Results of retrieval Protein name (UniProtKB/Swiss-Prot Accession number) |
| --- | --- |
| m/z 24,660 to 24,750 (protein J) | Transmembrane protein ENSP00000339174. (A6NI61), Protein Mis18-beta. (O43482), Cell death activator CIDE-A. (O60543), Acyl-protein thioesterase 1. (O75608), Acyl-protein thioesterase 2. (O95372), High mobility group protein B1. (P09429), Folate receptor alpha. (P15328), Ras-related protein Rab-3B. (P20337), Myelin P0 protein. (P25189), 60S ribosomal protein L10a. (P62906), UPF0418 protein FAM164B. (Q5TFG8), UPF0510 protein C19orf63. (Q5UCC4), Complement C1q-like protein 3. (Q5VWW1), Synaptonemal complex central element protein 2. (Q6PIF2), GLIPR1-like protein 1. (Q6UWM5), Putative uncharacterized protein FLJ43582. (Q6ZUL3), Putative triosephosphate isomerase-like protein LOC286016. (Q7Z6K2), Lipoma HMGIC fusion :partner-like 3 protein. (Q86UP9), ADP-ribosylation factor-like protein 6-interacting protein 6(Q8N6S5), C-type lectin domain family 4 member D. (Q8WXI8), Ras-related protein Rab-37. (Q96AX2), Pleckstrin homology domain-containing family B member 2(Q96CS7), GTP-binding protein Rit2. (Q99578), Programmed cell death protein 10. (Q9BUL8), COMM domain-containing protein 5. (Q9GZQ3), Homeobox protein MIXL1. (Q9H2W2), Protein Plunc. (Q9NP55), Kallikrein-14. (Q9P0G3), Nucleolar protein 12. (Q9UGY1), Cell death activator CIDE-B. (Q9UHD4), SERTA domain-containing protein 1. (Q9UHV2) |

TABLE 8

| Proteins or fragments thereof detected | Results of retrieval Protein name (UniProtKB/Swiss-Prot Accession number) |
| --- | --- |
| m/z 35,980 36,290 (protein K) | GATS-like protein 2. (A6NHX0), GATS-like protein 1. (A6NNH0), Transcription cofactor vestigial-like protein 3. (A8MV65), PDZ domain-containing protein GIPC1. (O14908), CD5 antigen-like. (O43866), Aldo-keto reductase family 1 member B10. (O60218), Ornithine carbamoyltransferase, mitochondrial. (P00480), Eukaryotic translation initiation factor 2 subunit 1. (P05198), L-lactate dehydrogenase C chain. (P07864), Annexin A3. (P12429), Heme oxygenase 2. (P30519), Killer cell immunoglobulin-like receptor 2DL1. (P43626), Killer cell immunoglobulin-like receptor 2DL2. (P43627), BRCA1/BRCA2-containing complex subunit 3. (P46736), Arginase-2, mitochondrial. (P78540), BCL2/adenovirus E1B 19 kDa protein-interacting protein 2. (Q12982), to Ankyrin repeat domain-containing protein 1. (Q15327), Renalase. (Q5VYX0), RNA (guanine-9-)-methyltransferase domain-containing protein 3. (Q6PF06), COP9 signalosome complex subunit 6. (Q7L5N1), Uncharacterized protein C2orf34. (Q7Z624), Olfactory receptor 2T4. (Q8NH00), GATS-like protein 3. (Q8WTX7), Tsukushin. (Q8WUA8), Thioredoxin domain-containing protein 15. (Q96J42), Lymphokine-activated killer T-cell-originated protein kinase. (Q96KB5), Mas-related G-protein coupled receptor member X1. (Q96LB2), Doublesex- and mab-3-related transcription factor B1. (Q96MA1), Uncharacterized protein C1orf198. (Q9H425), BRCA2 and CDKN1A-interacting protein. (Q9P287), Dickkopf-related protein 3. (Q9UBP4), Putative ribosomal RNA methyltransferase 1. (Q9UET6), |

TABLE 8-continued

| Proteins or fragments thereof detected | Results of retrieval Protein name (UniProtKB/Swiss-Prot Accession number) |
| --- | --- |
| | Putative ribosomal RNA methyltransferase 1. (Q9UET6), Zinc finger protein 330. (Q9Y3S2) |

TABLE 9

| Proteins or fragments thereof detected | Results of retrieval Protein name (UniProtKB/Swiss-Prot Accession number) |
| --- | --- |
| m/z 8,650 to 8,750 (protein L) | Putative transmembrane protein ENSP00000369095. (A6NJY4), Putative uncharacterized protein ENSP00000362624. (A6NLI3), Uncharacterized protein C21orf99-like. (A6NMZ6), Uncharacterized protein LOC388588. (B2RUZ4), Apolipoprotein A-II. (P02652), Basic nuclear protein HPS2. (P04554), Pulmonary surfactant-associated protein B. (P07988), C-C motif chemokine 2. (P13500), Uncharacterized protein C17orf67. (Q0P5P2), C-C motif chemokine 14. (Q16627), Embryonic stem cell-related gene protein. (Q1W209), UPF0731 protein C6orf225. (Q4GON7), Putative serine protease inhibitor Kazal- type 5-like 2. (Q6IE38), Saposin A-like (By similarity). (Q6NUJ1), Kunitz-type protease inhibitor 4. (Q6UDR6), Ly6/PLAUR domain-containing protein 2. (Q6UXB3), Putative uncharacterized protein UNQ5830/ PRO19650/PRO19816. (Q6UY13), UPF0729 protein C18orf32. (Q8TCD1), Probable protein BRICK1. (Q8WUW1), UPF0640 protein. (Q8WVIO), Calcium/calmodulin-dependent protein kinase II inhibitor 2. (Q96S95), Putative DPH3 homolog B. (Q9H4G8) |

TABLE 10

| Proteins or fragments thereof detected | Results of retrieval Protein name (UniProtKB/Swiss-Prot Accession number) |
| --- | --- |
| m/z 9,100 to 9,200 (protein M) | Cytochrome c oxidase subunit 7A3, mitochondrial. (O60397), Putative double homeobox protein 2. (O75505), Dolichol phosphate-mannose biosynthesis regulatory protein. (O94777), Lymphocyte antigen 6 complex locus protein G6c. (O95867), Lymphocyte antigen 6 complex locus protein G6d. (O95868), TC-2. (P02775), Saposin-A. (P07602), Saposin-D. (P07602), Putative DAP-2 like protein C8orf68. (P0C838), MDNCF-a. (P10145), U6 snRNA-associated Sm-like protein LSm6. (P62312), 40 S ribosomal protein S21. (P63220), Selenoprotein W. (P63302), Keratin-associated protein 19-4. (Q3LI73), Late cornified envelope protein 3A. (Q5TA76), Putative BMS1-like protein. (Q6IPT3), Protein FAM138A/B/C/F. (Q6VEP3), Protein ADMP. (Q8NFR3), V-type proton ATPase subunite 2. (Q8NHE4), Pancreatic progenitor cell differentiation and proliferation factor-like protein. (Q8WWR9), Beta-catenin-interacting protein 1. (Q9NSA3) |

TABLE 11

| Proteins or fragments thereof detected | Results of retrieval Protein name (UniProtKB/Swiss-Prot Accession number) |
|---|---|
| m/z 11,760 to 11,890 (protein N) | Ig kappa chain V-I region Lay. (P01605), Ig kappa chain V-I region Roy. (P01608), Ig kappa chain V-I region Mev. (P01612), Ig lambda chain V-II region BO. (P01710), Pterin-4-alpha-carbinolamine dehydratase. (P61457), Peptidyl-prolyl cis-trans isomerase FKBP1A. (P62942), Ig gamma lambda chain V-II region DOT. (P80422), Putative olfactory receptor-like protein ENSP00000367619. (Q3C1V7), Putative palmitoyltransferase ZDHHC8-like protein. (Q3KR32), Caspase recruitment domain-containing protein 17. (Q5XLA6), Insulin growth factor-like family member 4. (Q6B9Z1), Keratin-associated protein 5-6. (Q6L8G9), UPF0697 protein C8orf40. (Q96E16), Protein S100-A16. (Q96FQ6), C-Myc-binding protein. (Q99417), Thioredoxin, mitochondrial. (Q99757), Exocrine differentiation and proliferation factor. (Q9H3Y8), Sperm protein associated with the nucleus on the X chromosome B/F. (Q9NS25), Protein reprimo. (Q9NS64), Alpha-hemoglobin-stabilizing protein. (Q9NZD4), Transcription initiation factor IIA beta chain. (P52655), Death-associated protein-like 1. (A0PJW8), Putative glutaredoxin-like protein. (A6NLA2), High mobility group protein HMGI-C. (P52926), Apolipoprotein C-IV. (P55056), Protein TMEM155. (Q4W5P6), Putative uncharacterized protein FP588. (Q71RF5), Caspase-10 subunit p12. (Q92851), Transmembrane protein 141. (Q96145), DET1- and DDB1-associated protein 1. (Q9BW61), 39S ribosomal protein L20, mitochondrial. (Q9BYC9), 39S ribosomal protein L36, mitochondrial. (Q9P0J6), Signal peptidase complex subunit 1. (Q9Y6A9) |

Through the database searching, only one protein (Protein S100-A10) was retrieved as protein F (m/z: 11,020 to 11,120). Meanwhile, the present inventors previously disclosed that protein F (calcium-binding protein S100A10) can be used as a marker for determining sensitivity to L-OHP in a precedent patent application (WO 2009/96196) of the same inventors. Through the Examples herein, in addition to prediction of the sensitivity of a specimen to L-OHP before the treatment, protein F was found to also serve as a marker which can predict therapeutic response in an early stage after start of the treatment and which can be used in the case of 5-FU (single agent) or the case of a combination of 5-FU and L-OHP.

Example 5

In the database searching carried out in Example 4, only one protein (Protein S100A10) was retrieved as protein F (m/z: 11,020 to 11,120). Thus, expression of protein F in HCT116 and DLD-1 was confirmed.

1) Method

Through the same procedure as employed in Example 1, intracellular proteins were extracted from HCT116 cells and DLD-1 cells. In each case, the thus-extracted proteins were subjected to SDS-PAGE at constant 100 V. After completion of electrophoresis, the proteins were blotted onto a PVDF membrane and blocked. Then, primary antibody reaction was performed by use of an anti-S100A10 monoclonal antibody (Purified Mouse Anti-Annexin II light chain monoclonal antibody, BD Transduction Laboratories). Secondary antibody reaction was performed by use of an alkaline phosphatase-labeled anti-mouse IgG antibody. CDP-Star™ chemiluminescent substrate was added as a reaction substrate, and the target protein was detected by means of a lunino-image analyzer (LAS-4000mini, FUJIFILM).

(2) Results

Figure 13:
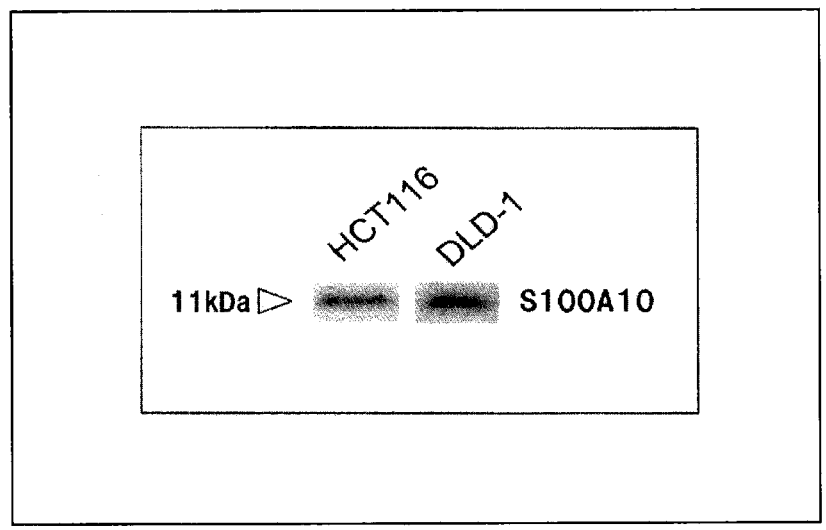
FIG. 13 A western blot feature showing detection of S100A10 in HCT116 cells and DLD-1 cells.

Expression of S100A10 detected in Example 1 as protein F (m/z: 11,020 to 11,120) in HCT116 and in DLD-1 was confirmed through the Western blotting technique employing an anti-S100A10 monoclonal antibody (FIG. 13).

The invention claimed is:

1. A method for determining sensitivity of a subject undergoing therapy for colorectal cancer with 5-fluorouracil or a salt thereof, the method comprising:

obtaining a sample (A) from the subject after being administered 5-fluorouracil of a salt thereof, identifying by mass spectrometry at least one peak selected from the group consisting of a peak at m/z of 5,300 to 5,400, a peak at m/z of 6,130 to 6,230, a peak at m/z of 7,000 to 7,080, a peak at m/z of 11,020 to 11,120, a peak at m/z of 17,100 to 17,270, a peak at m/z of 18,290 to 18,470, a peak at m/z of 24,660 to 24,750, a peak at m/z of 35,980 to 36,290, a peak at m/z of 7,840 to 7,920, and a peak at m/z of 9,100 to 9,200;

comparing the at least one peak intensity to a corresponding peak measured the same way from a sample (B) obtained from the subject prior to being administered 5-fluorouracil or a salt thereof and/or a corresponding peak of a predetermined standard peak intensity (C), and if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 11,020 to 11,120, a peak at m/z of 17,100 to 17,270, a peak at m/z of 18,290 to 18,470, a peak at m/z of 24,660 to 24,750, and a peak at m/z of 35,980 to 36,290 is higher than the intensity of the corresponding at least one peak at m/z of sample (B) and/or (C) ceasing administration of 5-fluorouracil or a salt thereof, if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 11,020 to 11,120, a peak at m/z of 17,100 to 17,270, a peak at m/z of 18,290 to 18,470, a peak at m/z of 24,660 to 24,750, and a peak at m/z of 35,980 to 36,290 is about the same or is lower than the intensity of the corresponding at least one peak at m/z of sample (B) and/or (C) continuing administration of 5-fluorouracil or a salt thereof, if the intensity of at least one of the peaks of sample (A) selected from the group consisting of a peak at m/z of 7,840 to 7,920, and a peak at m/z of 9,100 to 9,200 is lower than the intensity of the corresponding at least one peak at m/z of sample (B) and/or (C) continuing administration of 5-fluorouracil or a salt thereof, or if the intensity of at least one of the peaks of sample (A) selected from the group consisting of a peak at m/z of 7,840 to 7,920, and a peak at m/z of 9,100 to 9,200 is about the same or is higher than the intensity of the corresponding at least one peak at m/z of sample (B) and/or (C) ceasing administration of 5-fluorouracil or a salt thereof.

2. A method for determining sensitivity of a subject undergoing therapy for colorectal cancer with oxaliplatin, the method comprising:

obtaining a sample (A) from the subject after being administered oxaliplatin or a salt thereof, identifying by mass spectrometry at least one peak selected from the group consisting of a peak at m/z of 5,300 to 5,400, a peak at m/z of 6,130 to 6,230, a peak at m/z of 7,000 to 7,080, a peak at m/z of 12,440 to 12,560, a peak at m/z of 17,100 to 17,270, a peak at m/z of 18,290 to 18,470, a peak at m/z of 24,660 to 24,750, a peak at m/z of 35,980 to 36,290, a peak at m/z of 7,840 to 7,920, and a peak at m/z of 9,100 to 9,200;

comparing the at least one peak intensity to a corresponding peak measured the same way from a sample (B) obtained from the subject prior to being administered oxaliplatin or a salt thereof and/or a corresponding peak of a predetermined standard peak intensity (C), and if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 12,440 to 12,560, a peak at m/z of 17,100 to 17,270, a peak at m/z of 18,290 to 18,470, a peak at m/z of 24,660 to 24,750, and a peak at m/z of 35,980 to 36,290 is higher than the intensity of the corresponding at least one peak at m/z of sample (B) and/or (C) ceasing administration of oxaliplatin or a salt thereof, if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 12,440 to 12,560, a peak at m/z of 17,100 to 17,270, a peak at m/z of 18,290 to 18,470, a peak at m/z of 24,660 to 24,750, and a peak at m/z of 35,980 to 36,290 is about the same or is lower than the intensity of the corresponding at least one peak at m/z of sample (B) and/or (C) continuing administration of oxaliplatin or a salt thereof, if the intensity of at least one of the peaks of sample (A) selected from the group consisting of a peak at m/z of 7,840 to 7,920, and a peak at m/z of 9,100 to 9,200 is lower than the intensity of the corresponding at least one peak at m/z of sample (B) and/or (C) continuing administration of oxaliplatin or a salt thereof, or if the intensity of at least one of the peaks of sample (A) selected from the group consisting of a peak at m/z of 7,840 to 7,920, and a peak at m/z of 9,100 to 9,200 is about the same or is higher than the intensity of the corresponding at least one peak at m/z of sample (B) and/or (C) ceasing administration of oxaliplatin or a salt thereof.

3. A method for determining sensitivity of a subject undergoing therapy for colorectal cancer with a combination of 5-fluorouracil or a salt thereof and oxaliplatin or a salt thereof, the method comprising:

obtaining a sample (A) from the subject after being administered 5-fluorouracil or a salt thereof and oxaliplatin or a salt thereof, identifying by mass spectrometry at least one peak selected from the group consisting of a peak at m/z of 5,300 to 5,400, a peak at m/z of 6,130 to 6,230, a peak at m/z of 7,000 to 7,080, a peak at m/z of 11,020 to 11,120, a peak at m/z of 17,100 to 17,270, a peak at m/z of 18,290 to 18,470, a peak at m/z of 24,660 to 24,750, a peak at m/z of 35,980 to 36,290, a peak at m/z of 7,840 to 7,920, a peak at m/z of 9,100 to 9,200, a peak at m/z of 8,920 to 9,000, and a peak at m/z of 12,440 to 12,560;

comparing the at least one peak intensity to a corresponding peak measured the same way from a sample (B) obtained from the subject prior to being administered 5-fluorouracil or a salt thereof and oxliplatin or a salt thereof and/or a corresponding peak of a predetermined standard peak intensity (C), and if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 11,020 to 11,120, a peak at m/z of 17,100 to 17,270, a peak at m/z of 18,290 to 18,470, a peak at m/z of 24,660 to 24,750, and a peak at m/z of 35,980 to 36,290 is higher than the intensity of the corresponding at least one peak at m/z of sample (B) and/or (C) ceasing administration of 5-fluorouracil or a salt thereof and oxaliplatin or a salt thereof, if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 11,020 to 11,120, a peak at m/z of 17,100 to 17,270, a peak at m/z of 18,290 to 18,470, a peak at m/z of 24,660 to 24,750, and a peak at m/z of 35,980 to 36,290 is about the same or is lower than the intensity of the corresponding at least one peak at m/z of sample (B) and/or (C) continuing administration of 5-fluorouracil or a salt thereof and oxaliplatin or a salt thereof, if the intensity of at least one of the peaks of sample (A) selected from the group consisting of a peak at m/z of 7,840 to 7,920, and a peak at m/z of 9,100 to 9,200 is lower than the intensity of the corresponding at least one peak at m/z of sample (B) and/or (C) continuing administration of 5-fluorouracil or a salt thereof and oxaliplatin or a salt thereof, if the intensity of at least one of the peaks of sample (A) selected from the group consisting of a peak at m/z of 7,840 to 7,920, and a peak at m/z of 9,100 to 9,200 is about the same or is higher than the intensity of the corresponding at least one peak at m/z of sample (B) and/or (C) ceasing administration of 5-fluorouracil or a salt thereof and oxaliplatin or a salt thereof, if the intensity of at least one of the peaks of sample (A) selected from the group consisting a peak at m/z of 8,920 to 9,000, and a peak at m/z of 12,440 to 12,560 is higher than the intensity of the corresponding at least one peak at m/z of sample (B) and/or (C) continuing administration of 5-fluorouracil or a salt thereof and oxaliplatin or a salt thereof, or if the intensity of at least one of the peaks of sample (A) selected from the group consisting a peak at m/z of 8,920 to 9,000, and a peak at m/z of 12,440 to 12,560 is about the same or is lower than the intensity of the corresponding at least one peak at m/z of sample (B) and/or (C) ceasing administration of 5-fluorouracil or a salt thereof and oxaliplatin or a salt thereof.

4. The method of claim 1, wherein if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 11,020 to 11,120, a peak at m/z of 17,100 to 17,270, a peak at m/z of 18,290 to 18,470, a peak at m/z of 24,660 to 24,750, and a peak at m/z of 35,980 to 36,290 is higher than the intensity of the corresponding at least one peak at m/z of sample (B) and/or (C) ceasing administration of 5-fluorouracil or a salt thereof.

5. The method of claim 1, wherein if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 11,020 to 11,120, a peak at m/z of 17,100 to 17,270, a peak at m/z of 18,290 to 18,470, a peak at m/z of 24,660 to 24,750, and a peak at m/z of 35,980 to 36,290 is about the same or is lower than the intensity of the corresponding at least one peak at m/z of sample (B) and/or (C) continuing administration of 5-fluorouracil or a salt thereof.

6. The method of claim 1, wherein if the intensity of at least one of the peaks of sample (A) selected from the group consisting of a peak at m/z of 7,840 to 7,920, and a peak at m/z of 9,100 to 9,200 is lower than the intensity of the corresponding at least one peak at m/z of sample (B) and/or (C) continuing administration of 5-fluorouracil or a salt thereof.

7. The method of claim 1, wherein if the intensity of at least one of the peaks of sample (A) selected from the group consisting of a peak at m/z of 7,840 to 7,920, and a peak at m/z of 9,100 to 9,200 is about the same or is higher than the intensity of the corresponding at least one peak at m/z of sample (B) and/or (C) ceasing administration of 5-fluorouracil or a salt thereof.

8. The method of claim 2, wherein if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 12,440 to 12,560, a peak at m/z of 17,100 to 17,270, a peak at m/z of 18,290 to 18,470, a peak at m/z of 24,660 to 24,750, and a peak at m/z of 35,980 to 36,290 is higher than the intensity of the corresponding at least one peak at m/z of sample (B) and/or (C) ceasing administration of oxaliplatin or a salt thereof.

9. The method of claim 2, wherein if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 12,440 to 12,560, a peak at m/z of 17,100 to 17,270, a peak at m/z of 18,290 to 18,470, a peak at m/z of 24,660 to 24,750, and a peak at m/z of 35,980 to 36,290 is about the same or is lower than the intensity of the corresponding at least one peak at m/z of sample (B) and/or (C) continuing administration of oxaliplatin or a salt thereof.

10. The method of claim 2, wherein if the intensity of at least one of the peaks of sample (A) selected from the group consisting of a peak at m/z of 7,840 to 7,920, and a peak at m/z of 9,100 to 9,200 is lower than the intensity of the corresponding at least one peak at m/z of sample (B) and/or (C) continuing administration of oxaliplatin or a salt thereof.

11. The method of claim 2, wherein if the intensity of at least one of the peaks of sample (A) selected from the group consisting of a peak at m/z of 7,840 to 7,920, and a peak at m/z of 9,100 to 9,200 is about the same or is higher than the intensity of the corresponding at least one peak at m/z of sample (B) and/or (C) ceasing administration of oxaliplatin or a salt thereof.

12. The method of claim 3, wherein if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 11,020 to 11,120, a peak at m/z of 17,100 to 17,270, a peak at m/z of 18,290 to 18,470, a peak at m/z of 24,660 to 24,750, and a peak at m/z of 35,980 to 36,290 is higher than the intensity of the corresponding at least one peak at m/z of sample (B) and/or (C) ceasing administration of 5-fluorouracil or a salt thereof and oxaliplatin or a salt thereof.

13. The method of claim 3, wherein if the intensity of at least one of the peaks of sample (A) selected from the group consisting of a peak at m/z of 5,300 to 5,400, a peak at m/z of 6,130 to 6,230, a peak at m/z of 7,000 to 7,080, a peak at m/z of 11,020 to 11,120, a peak at m/z of 17,100 to 17,270, a peak at m/z of 18,290 to 18,470, a peak at m/z of 24,660 to 24,750, and a peak at m/z of 35,980 to 36,290 is about the same or is lower than the intensity of the corresponding at least one peak at m/z of sample (B) and/or (C) continuing administration of 5-fluorouracil or a salt thereof and oxaliplatin or a salt thereof.

14. The method of claim 3, wherein if the intensity of at least one of the peaks of sample (A) selected from the group consisting of a peak at m/z of 7,840 to 7,920, and a peak at m/z of 9,100 to 9,200 is lower than the intensity of the corresponding at least one peak at m/z of sample (B) and/or (C) continuing administration of 5-fluorouracil or a salt thereof and oxaliplatin or a salt thereof.

15. The method of claim 3, wherein if the intensity of at least one of the peaks of sample (A) selected from the group consisting of a peak at m/z of 7,840 to 7,920, and a peak at m/z of 9,100 to 9,200 is about the same or is higher than the intensity of the corresponding at least one peak at m/z of sample (B) and/or (C) ceasing administration of 5-fluorouracil or a salt thereof and oxaliplatin or a salt thereof.

16. The method of claim 3, wherein if the intensity of at least one of the peaks of sample (A) selected from the group consisting a peak at m/z of 8,920 to 9,000, and a peak at m/z of 12,440 to 12,560 is higher than the intensity of the corresponding at least one peak at m/z of sample (B) and/or (C) continuing administration of 5-fluorouracil or a salt thereof and oxaliplatin or a salt thereof.

17. The method of claim 3, wherein if the intensity of at least one of the peaks of sample (A) selected from the group consisting a peak at m/z of 8,920 to 9,000, and a peak at m/z of 12,440 to 12,560 is about the same or is lower than the intensity of the corresponding at least one peak at m/z of sample (B) and/or (C) ceasing administration of 5-fluorouracil or a salt thereof and oxaliplatin or a salt thereof.

18. A method for determining sensitivity of a subject prior to undergoing therapy for colorectal cancer with 5-fluorouracil or a salt thereof, oxaliplatin or a salt thereof, or a combination of 5-fluorouracil or a salt thereof and oxaliplatin or a salt thereof, the method comprising:
  obtaining a sample (B) from the subject prior to being administered 5-fluorouracil or a salt thereof, oxaliplatin or a salt thereof, or a combination of 5-fluorouracil or a salt thereof and oxaliplatin or a salt thereof,
  identifying by mass spectrometry at least one peak selected from the group consisting of a peak at m/z of 6,130 to 6,230, a peak at m/z of 8,650 to 8,750, a peak at m/z of 11,760 to 11,890, and a peak at m/z of 17,100 to 17,270;
  comparing the at least one peak intensity to a corresponding peak of a predetermined standard peak intensity (C), and
  if the intensity of at least one of the peaks of sample (B) selected from the group consisting of a peak at m/z of 6,130 to 6,230, a peak at m/z of 8,650 to 8,750, a peak at m/z of 11,760 to 11,890, and a peak at m/z of 17,100 to 17,270 is lower than the intensity of the corresponding peak of a predetermined standard peak intensity (C) ceasing administration of 5-fluorouracil or a salt thereof, oxaliplatin or a salt thereof, or a combination of 5-fluorouracil or a salt thereof and oxaliplatin or a salt thereof,
  if the intensity of at least one of the peaks of sample (B) selected from the group consisting of a peak at m/z of 6,130 to 6,230, a peak at m/z of 8,650 to 8,750, a peak at m/z of 11,760 to 11,890, and a peak at m/z of 17,100 to 17,270 is higher than the intensity of the corresponding peak of a predetermined standard peak intensity (C) continuing administration of 5-fluorouracil or a salt thereof, oxaliplatin or a salt thereof, or a combination of 5-fluorouracil or a salt thereof and oxaliplatin or a salt thereof.

19. The method of claim 18, wherein if the intensity of at least one of the peaks of sample (B) selected from the group consisting of a peak at m/z of 6,130 to 6,230, a peak at m/z of 8,650 to 8,750, a peak at m/z of 11,760 to 11,890, and a peak at m/z of 17,100 to 17,270 is lower than the intensity of the corresponding peak of a predetermined standard peak intensity (C) ceasing administration of 5-fluorouracil or a salt thereof, oxaliplatin or a salt thereof, or a combination of 5-fluorouracil or a salt thereof and oxaliplatin or a salt thereof.

20. The method of claim 18, wherein if the intensity of at least one of the peaks of sample (B) selected from the group consisting of a peak at m/z of 6,130 to 6,230, a peak at m/z of 8,650 to 8,750, a peak at m/z of 11,760 to 11,890, and a peak at m/z of 17,100 to 17,270 is higher than the intensity of the corresponding peak of a predetermined standard peak intensity (C) continuing administration of 5-fluorouracil or a salt thereof, oxaliplatin or a salt thereof, or a combination of 5-fluorouracil or a salt thereof and oxaliplatin or a salt thereof.

\* \* \* \* \*